United States Patent
Denlinger et al.

(10) Patent No.: US 7,560,243 B2
(45) Date of Patent: Jul. 14, 2009

(54) WHITE BLOOD CELL FUNCTIONAL ASSAY

(75) Inventors: Loren C. Denlinger, Madison, WI (US); Kirk J. Hogan, Madison, WI (US); Paul J. Bertics, Oregon, WI (US); Kathleen Schell, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 589 days.

(21) Appl. No.: 10/827,718

(22) Filed: Apr. 20, 2004

(65) Prior Publication Data
US 2004/0253650 A1 Dec. 16, 2004

Related U.S. Application Data

(60) Provisional application No. 60/464,231, filed on Apr. 21, 2003.

(51) Int. Cl.
*G01N 33/00* (2006.01)
(52) U.S. Cl. .................. 435/7.24; 435/6; 435/40.5; 435/287.2; 435/372; 422/61; 422/73; 436/517; 436/538; 436/548; 436/56; 436/63; 436/172; 436/175
(58) Field of Classification Search .................. 435/2, 435/3, 6, 7.2, 7.24, 40.5, 383, 287.2, 372; 422/61, 73; 436/517, 538, 548, 63, 172, 436/56, 175
See application file for complete search history.

(56) References Cited

U.S. PATENT DOCUMENTS 4,444,879 A * 4/1984 Foster et al. ............... 435/7.95

OTHER PUBLICATIONS

Aga et al., Modulation of monocyte signaling and pore formation in response to agonists of the nucleotide receptor P2X7, Journal of Leukocyte Biology 72: 222-232 (Jul. 2002).*
Michel et al., Ion effects on human recombinant P2X7 receptor function, (Naunyn-Schmiedeberg's Arch Pharmacol 359: 102-109 (1999).*
Watters, J. J. et al. (2001). Drug Develop Res. 53:91-104.
Di Virgilio, F. et al. (2001). Blood 97(3):587-600.
Proctor, R. A. et al. (1994). Proceedings of the Natl. Acad. of Sci. of the U.S.A. 91(13):6017-20.

(Continued)

*Primary Examiner*—Gailene R Gabel
(74) *Attorney, Agent, or Firm*—Quarles & Brady LLP

(57) ABSTRACT

A method of rapidly assaying nucleotide receptor $P2X_7$ pore activity in white blood cells contained within a blood sample. A method according to the invention includes the steps of: (a) labeling the white blood cells with a white blood cell-specific label; (b) depolarizing the labeled white blood cells with an isotonic depolarizing solution; (c) contacting the labeled white blood cells with a dye and a $P2X_7$ agonist in an amount sufficient to activate nucleotide receptor $P2X_7$ pore activity; (d) contacting the labeled white blood cells with a divalent cation in an amount sufficient to deactivate nucleotide receptor $P2X_7$ pore activity; and (e) analyzing dye uptake in labeled white blood cells whereby nucleotide receptor $P2X_7$ pore activity is quantified by the amount of dye taken up in labeled white blood cells treated with $P2X_7$ agonist relative to labeled white blood cells in the absence of $P2X_7$ agonist.

19 Claims, 6 Drawing Sheets

OTHER PUBLICATIONS

Solle, M. et al. (2001). J Biol Chem 276(1):125-32.
Aga, M. et al. (2002). J. Leukocyte Biol. 72:222-232.
Surprenant, A. et al. (1996). Science 272(5262):735-8.
Gu, B. J. et al. (2001). J Biol Chem 276(14)11135-11142.
Denlinger, L. C. et al. (2001). J Immunol 167:1871-1876.
Humphreys, B. D. et al. (1996). J Immunol 157(12):5627-5637.
Adriouch, S. et al. (2002). J Immunol 169:4108-4112.
Wiley, J. S. et al. (2003). Journal of Biological Chemistry 278:17108.
Ferrari, D. et al. (1997). Journal of Cell Biology 139:1635.
Gogos, C. A. et al. (2000). Journal of Infectious Diseases 181:176.
Li, C. M. et al. (2002). Journal of Infectious Diseases 186-1458.
Thunberg, U. et al. (2002). Lancet. 360:1935.
Li, C. M. et al. (2002). FEBS Letters 531:127.
Wiley, J. S. et al. (2002). Lancet. 359-1114.
Lammas, D. A. et al. (1997). Immunity. 7:433-444.
Ferrari, D. et al. (1997). J Exp Med 185:579.
Beigi, R. D. et al. (2000). J Immunol 165:7189.
Sluyter, R. et al. (2004). J Immunol 172:3399.
Wilkin, F. et al. (2002). European Journal of Immunology. 32:2409.
Budagian, V. et al. (2003). Journal of Biological Chemistry 278-1549.
Ferrari, D. et al. (1999). Journal of Biological Chemistry 274:13205.
Labasi, J. M. et al. (2002). Journal of Immunology 168:6436.
Chused, Thomas M., et al., J. Immunology, 1996, 157:1371-1380.
Hickman, Suzanne E., et al., Blood, 1994, 84(8):2452-2456.
Nagy, Péter, et al., Imm. Letters, 1995, 44:91-95.
Nihei, Oscar K., et al., Mem. Inst. Oswaldo Cruz, 2000, 95(3):415-428.
Wiley, James S., et al., Arch. Biochem. and Biophysics, 1993, 305(1):54-60.
Wiley, James S., et al., Leukemia, 1994, 8(1):181-185.
Wiley, James S., et al., Am. Physiological Soc., 1998, C1224-C1231.

* cited by examiner

WHITE BLOOD CELL FUNCTIONAL ASSAY

CROSS-REFERENCE TO RELATED APPLICATION

This application claims the benefit of U.S. Provisional application 60/464,231, filed Apr. 21, 2003, incorporated herein by reference.

STATEMENT AS TO RIGHTS TO INVENTIONS MADE UNDER FEDERALLY SPONSORED RESEARCH OR DEVELOPMENT

This work was supported in part by grants from the National Institutes of Health Al 34891. The Government of the United States of America may have certain rights in this invention.

FIELD OF THE INVENTION

This invention relates generally to biomedical assays. In particular, this invention is directed to methods for rapidly assaying pore activity of the nucleotide receptor $P2X_7$.

BACKGROUND OF THE INVENTION

As used herein, septic shock refers to a systemic immune system dysfunction in response to an overwhelming infection leading to hypotension and organ failure (1). Over 750,000 cases of severe sepsis (the precursor to shock) occur each year in the United States with an overall mortality rate of 28%, making the number of deaths similar to that from coronary artery disease (2). Because early intervention with supportive therapies makes a difference in outcome (3), means to prospectively stratify patients on the basis of risk has become one of the central objectives in the sepsis field (1, 4). The failure of numerous clinical trials of immunomodulatory therapeutics over the past few decades, some of which actually showing higher mortality in the therapeutic arm of the study, highlights the long felt need for improved prognostic indicators. These trials have demonstrated that there is significant patient-to-patient diversity of immune responses during severe sepsis, an aspect that has been poorly explained in the clinical literature (1, 4).

A novel signaling pathway pertinent to sepsis pathophysiology has recently been identified with global control over monocyte and macrophage inflammatory mediator production and microbial killing (5, 6). Specifically, extracellular adenine nucleotides, such as ATP, are released systemically by the adrenal gland, as well as locally by platelet degranulation and/or by cell death during the inflammatory response in sepsis. These hormones modulate monocyte and macrophage immune responses via interaction with the nucleotide receptor $P2X_7$ (5). The $P2X_7$ receptor controls the production of inflammatory mediators during sepsis, including tumor necrosis factor-alpha (TNF-alpha), interleukin-1beta (IL-1beta), IL-6, nitric oxide (NO), tissue factor, and prostaglandins (7-12). $P2X_7$-knockout mice exhibit greatly attenuated production of IL-1beta and IL-6 in response to endotoxin (lipopolysaccharide, LPS) (11), a common pathogenic agent in severe sepsis. Additionally, $P2X_7$ stimulation promotes membrane fusion events such as phagolysosomal maturation necessary for microbial killing, microvesicle generation required for IL-1beta processing, and giant cell formation needed to make granulomas (13-15). Finally, co-administration of the ATP analogue, 2-methylthio-ATP, protects mice from endotoxic death in an animal model of severe sepsis with concomitant reductions in LPS-induced serum levels of TNF-alpha and IL-1 (7). Thus, extracellular adenine nucleotides and the nucleotide receptor $P2X_7$ have a profound influence on monocyte and macrophage immune responses relevant to sepsis pathophysiology.

The family of P2 receptors binds extracellular nucleotides with two or more phosphates and has been divided into the P2X and P2Y subfamilies according to whether the individual member acts as an ion channel or a G-protein coupled receptor, respectively (6). $P2X_7$ belongs to the P2X family on the basis of structural similarity with the six other members, each with two predicted membrane spanning domains (6, 16). Whereas ligand-gated, nonselective cation channel activity is a common feature of the P2X family, reversible permeability to larger molecules (<900 Da) is a more characteristic feature of $P2X_7$ under biological conditions (6).

The gene for human $P2X_7$ contains two previously-described single nucleotide polymorphisms (SNPs) associated with functionally significant amino acid substitutions. Gu et al. have shown that the human $P2X_7$ gene contains a nucleotide polymorphism (SNP, A1513C) conferring an amino acid substitution that disrupts the pore activity of this receptor. In addition, Wiley et al. report that a Ti 729A mutation is associated with reduced pore activity due to a trafficking defect (Wiley et al. *J. Biol. Chem.* 278:17108-17113(2003)).

Because the $P2X_7$ pore activity and has been linked to monocyte and macrophage inflammatory mediator production (particularly IL-beta (14)), and because inflammatory mediator production is a major determinant in deciding on courses of immunosuppressive and anti-inflammatory therapies in the clinical setting, it is particularly desirable to obtain a rapid and convenient clinical assay for determining $P2X_7$ pore activity. A rapid assay of $P2X_7$ pore activity is therefore required to make reliable prognoses and refined therapeutic interventions.

Unfortunately, presently-known $P2X_7$ pore assays do not provide rapid and robust procedures for use outside of the laboratory setting, most notably in the clinical setting. For example, Gu et al., (see *J. Biol. Chem.* 276, 11135-11142), in describing the Al 513C polymorphism, provide a $P2X_7$ pore assay based on ethidium bromide uptake in ATP induced monocytes. A similar assay was utilized by Wiley et al. in analyzing the T1729A polymorphism. However, this assay requires extensive isolation and purification of these cells apart from other cell types before dye influx can be measured by time-resolved flow cytometry. In particular, this method requires the use of a ficoll hypaque density gradient to obtain the necessary monocytes. The preparatory step is therefore time-consuming and, due to the technical aspects related to density gradient separation, not practical in the clinical setting where complex bench and cold room facilities are not available. The time necessary to carry out this technique is estimated to be at least one full workday for one skilled in the field with multiple sample processing not easily amendable to automation. Moreover, the volume of blood needed for the previous $P2X_7$ pore assay (i.e., several hundred cc's) precludes testing in pediatric and frail subjects.

As well, Patent Application US 2002/0182646 A1, published Dec. 5, 2002 to Ke et al., describes a method for measuring $P2X_7$ receptor-mediated macromolecule uptake in macrophages. Like the prior method of Gu et al., this approach also relies on complex preparatory steps to provide isolated and purified macrophages before pore activities may be reliably measured. Specifically, Ke et al. teach that macrophages are harvested from the peritoneal cavity of animals (e.g., mice) by medium injection into the cavity, followed by collection of the lavage fluid. Quite obviously, this approach does not provide a practical clinical procedure for rapid measurement of $P2X_7$ pore activity in humans.

Based upon the above-described needs and others, it is therefore desirable to obtain a rapid $P2X_7$ pore assay suitable for, but no limited to, use in the clinical setting. This assay would dispense with the time-consuming and technical complexities of previous methods. Preferably, the assay could be carried out directly on clinical specimens, for example, whole blood samples. Furthermore, the assay would provide improved sensitivity, reliability and robustness while, at the same time, being amendable to automation.

SUMMARY OF THE INVENTION

In one embodiment, the present invention provides a method of rapidly assaying nucleotide receptor $P2X_7$ pore activity in white blood cells. The method is particularly suited for, but not limited to, practice in the clinical setting and includes the steps of: (a) labeling white blood cells with a white blood cell-specific label; (b) depolarizing the labeled white blood cells in an isotonic depolarizing solution; (c) contacting the labeled white blood cells with a dye and a $P2X_7$ agonist in an amount sufficient to activate nucleotide receptor $P2X_7$ pore activity; (d) contacting the labeled white blood cells with a divalent cation in an amount sufficient to deactivate nucleotide receptor $P2X_7$ pore activity; and (e) analyzing dye uptake in labeled white blood cells whereby nucleotide receptor $P2X_7$ pore activity is quantified by the amount of dye taken up in labeled white blood cells treated with the $P2X_7$ agonist relative to labeled white blood cells in the absence of the $P2X_7$ agonist.

The above-described embodiment is preferably practiced on whole blood samples, of which white blood cells make up a minor fraction, setting the present method advantageously apart from any previously known $P2X_7$ pore assay. Isolation and purification of white blood cells apart from other cell types is unnecessary thereby conferring a significant advantage over previous techniques.

In a preferred embodiment, the white blood cell-specific label is a phycoerythrin-conjugated anti-CD14 antibody recognizing human monocytes and the dye is a macromolecule DNA-binding dye having a mass of less than approximately 900 Daltons, most preferably, the DNA-binding dye YO-PRO-1.

In a particularly preferred embodiment, the isotonic depolarizing solution includes the glutamate ion and, furthermore, sodium and chloride ions and divalent cations are absent from the isotonic depolarizing solution in amounts effective to inhibit $P2X_7$ pore activity.

The $P2X_7$ agonist useful in the invention are selected from the group consisting of 2',3'-O-(4-benzoyl)benzoyl-adenosine 5'-triphosphate (Bz-ATP), adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5'(beta,gamma-imido)triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof. In certain embodiments, the divalent cation is magnesium ion.

In preferred embodiments, dye uptake in step (e) is measured by flow cytometry. Flow cytometry detects labeled white blood cells apart from non-labeled cells and measures intensity of the dye taken up by the labeled white blood cells whereby nucleotide receptor $P2X_7$ pore activity is quantified by the amount of dye taken up in labeled white blood cells treated with the $P2X_7$ agonist relative to labeled white blood cells in the absence of said $P2X_7$ agonist.

The present invention is also a method of assaying nucleotide receptor $P2X_7$ pore activity in a blood sample including white blood cells, comprising the steps of: (a) labeling white blood cells included within the blood sample with a white blood cell-specific label; (b) depolarizing the labeled white blood cells in an isotonic depolarizing solution; (c) contacting the labeled white blood cells with a dye and a $P2X_7$ agonist in an amount sufficient to activate nucleotide receptor $P2X_7$ pore activity; (d) contacting the labeled white blood cells with a divalent cation in an amount sufficient to deactivate nucleotide receptor $P2X_7$ pore activity; and (e) analyzing dye uptake in labeled white blood cells of step (d) whereby nucleotide receptor $P2X_7$ pore activity is quantified by the amount of dye taken up in labeled white blood cells treated with the $P2X_7$ agonist relative to labeled white blood cells in the absence of the $P2X_7$ agonist.

In yet another embodiment, the invention provides a method of identifying a nucleotide receptor $P2X_7$-related molecular phenotype useful as a prognostic determinant of a clinical outcome in a patient, comprising the steps of: (a) carrying out an assay according to the invention on white blood cell samples from a patient population having known clinical outcomes to determine a plurality of receptor $P2X_7$ pore activities; and (b) correlating the nucleotide receptor $P2X_7$ pore activities with the known clinical outcomes to determine statistically significant correlations between respective pore activities and known clinical outcomes thereby determining a particular nucleotide receptor $P2X_7$ molecular phenotype useful as a prognostic determinant in a patient.

A further embodiment of the invention is directed to a method of identifying a nucleotide receptor $P2X_7$-related polymorphism useful as a prognostic determinant of a clinical outcome in a patient, comprising the steps of: (a) carrying out a pore assay according to the invention on white blood cell samples from a patient population having known clinical outcomes to determine a plurality of respective receptor $P2X_7$ pore activities; (b) correlating said nucleotide receptor $P2X_7$ pore activities with the known clinical outcomes to determine statistically significant correlations between respective pore activities and known clinical outcomes; and (c) characterizing genomic material from respective patients in which statistically significant correlations were identified in step (b) to identify a nucleotide receptor $P2X_7$-related polymorphism useful as a prognostic determinant.

The invention also encompasses methods of providing immunomodulatory and/or immunosuppressive as well as anti-infectious therapy to a patient, comprising the steps of: (a) analyzing a white blood sample from the patient by a pore assay according to the invention to obtain a nucleotide receptor $P2X_7$ pore activity for said patient; and (b) comparing said nucleotide receptor $P2X_7$ pore activity with previously-determined nucleotide receptor $P2X_7$ pore activities that demonstrate statistically significant correlation to clinical outcomes; and (c) based upon the result of step (b), providing therapy to either avoid or achieve a particular clinical outcome in the patient.

Other objects, features and advantages of the present invention will become apparent after review of the specification, claims and drawings.

DETAILED DESCRIPTION OF THE INVENTION

I. In General

Figure 1:
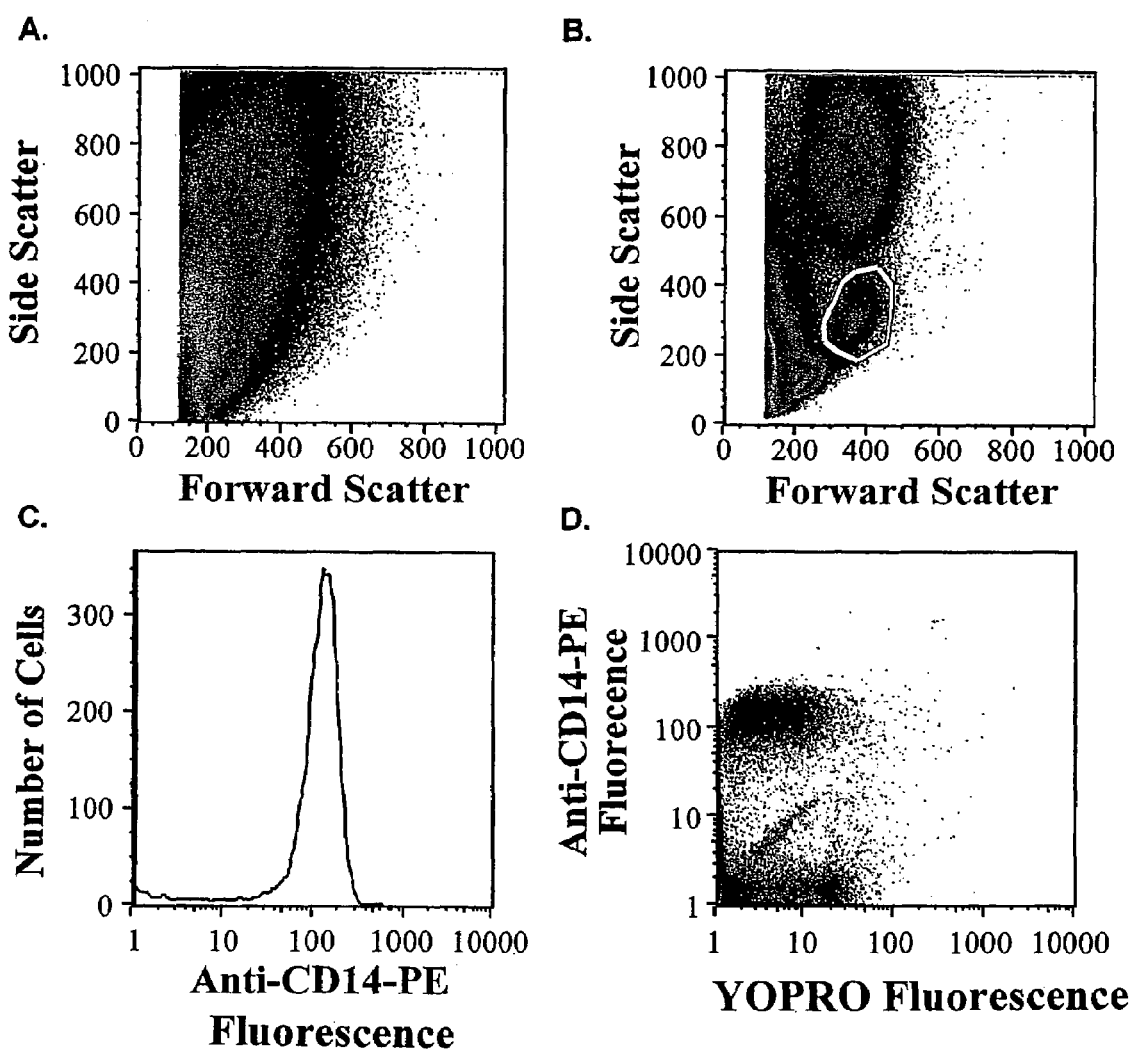
FIG. 1 displays data related to derivation of instrument settings for the washed whole blood pore assay. Panel A demonstrates the inability to discriminate monocytes by size (forward scatter) and granularity (side scatter) in the presence of an overwhelming number of RBCs and platelets. Mononuclear cells derived after one round of RBC lysis (Panel B) display the characteristic scatter associated with granulocytes, monocytes and lymphocytes. The circle, or gate, denotes the approximate position assumed by monocytes. The shading in panels A and B is reflective of increasing cell number, dark to light. Gated cells are shown in the Panel C to express CD14, a monocyte marker. Baseline YO-PRO-1 fluorescence associated with CD14+monocytes is then set as low as possible (Panel D) to maximize the potential fold increase in the Bz-ATP induced signal.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention that will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

Terms and abbreviations used throughout include:

"2-MeS-ATP" refers to 2-methylthio-adenosine triphosphate.

"Allele" refers to different copies of the same gene within a population that contain small differences in DNA sequence, usually resulting in functional variability.

"Anti-inflammatory cytokine" refers to an immune cell-derived protein that down regulates the effects of inflammatory cytokines, promotes immune cell differentiation, and assists in antibody generation. Examples include interleukin-4, IL-6, and IL-10.

"Bacteremia" refers to a bacterial infection of the blood.

"Bz-ATP" refers to 2',3'-O-(4-benzoyl)benzoyl-adenosine triphosphate.

"CD14" refers to a glycosylphosphatidyl inositol-linked cell surface protein expressed on monocytes and macrophages that acts as a high affinity receptor for LPS.

"Clinical outcome" refers to an observed result or consequence of medical treatment provided to a patient.

"Genotype" refers to the genetic sum of all alleles of a particular gene contained on all chromosomes leading to homozygous of heterozygous states. For example, if there is one copy of a gene per chromosome and two alleles in a population, there can be three genotypes A/A, A/B, and B/B.

"Hardy Weinberg equilibrium" refers to a genetic principle that allows for the prediction of the frequencies of genotypes within a population given the allele frequency. For example the genotypic frequencies of a monogenic trait with two alleles can be predicted by using the formula $f=a^2+2ab+b^2$, where a and b are the allele frequencies. These calculations allow for a determination of recruitment bias within a sample of a population.

"Inflammatory cytokine" refers to an immune cell-derived protein that promotes local and systemic responses to infection including the recruitment of inflammatory cells and/or direct microbicidal activity. Overabundance of these cytokines is associated with vascular damage resulting in the capillary leakage leading to septic shock. Examples include tumor necrosis factor-alpha (TNF-alpha), interleukin-1beta (IL-1beta), IL-12, and interferons.

"LPS" refers to lipopolysaccharide, the major glycolipid constituent of the outer leaflet of the outer membrane of Gram-negative bacteria.

"Locus" refers to a region of DNA containing multiple genes that is co-inherited.

"Monocyte" refers to a peripheral blood mononuclear cell that produces inflammatory and anti-inflammatory cytokines in response to LPS "Macrophage" refers to phagocytic cells derived from monocytes that are found in tissue compartments, also a major source of cytokine production.

"$P2X_7$" refers to the seventh member of the P2X family of nucleotide receptors, a multimeric nonselective cation channel that can also form a large pore allowing passage of molecules smaller than 900 Da.

"Phenotype" refers to observed variation in characteristics that result from the interactions of an organism's genotype and its environment.

"Prognosis" refers to a prediction of a probable course and outcome of a disease.

"Septic shock" refers to hypotension and organ failure as a result of immune system dysfunction in the presence of an overwhelming infection, usually accompanied by fever, tachycardia, tachypnea, and leukocytosis. Severe sepsis is thought to be a precursor to septic shock consisting of the above manifestations with hypotension or organ failure (not both).

"Single nucleotide polymorphism" or "SNP" refer to an allelic difference that occurs as the result of a change in a single base pair within the gene in question.

As used herein, "subject" or "patient" shall refer to a mammal, preferably but not limited to a human.

"TLR4" refers to the Toll-like Receptor 4, the major transmembrane signaling component of the CD14-dependent LPS receptor system.

II. The Invention

The present inventors have focused on disorders that arise from aberrant tissue responses to inflammation that may be traced to polymorphisms within genes encoding and regulating cytokine mediators. The inventors' overall aim is to identify alleles in distinct constituents of the host immune response that, as deleterious markers of the risk and severity of sepsis, may be of value in guiding immunosuppressive and anti-infectious therapy based on genetic idiosyncrasy. Accordingly, the inventors have analyzed polymorphisms in the monocyte purinergic receptor $P2X_7$ with a newly devised functional pore assay disclosed and claimed herein.

Availability of an improved pore assay according to the invention has several immediate impacts from the genomic perspective. First, it enables genomic data from distinct ethnic groups to be compared in international laboratories lacking access to the more challenging and costly method which has been previously described (Gu et al., 2001). This type of phenotypic data is critical to accurate interpretation of a given mutation within diverse genetic backgrounds. Second, the improved pore assay serves as a compass pointing to the identification of, for example, polymorphisms valuable as prognostic determinants in potential patient populations. In this regard, examples set forth below describe volunteer human subjects who exhibit reduced $P2X_7$ pore activity despite homozygous or heterozygous absence of two known mutations, suggesting that additional functionally important $P2X_7$ mutations remain to be discovered. Indeed, description of such additional mutations whose identification was made possible by the present invention is provided below in the final example. Third, the improved pore assay serves as an essential tool bridging the gap between laboratory bench and the bedside. Because of its capacity to integrate the influence of environmental factors and polymorphisms at other loci, a molecular phenotype improves the predictive value of personal genomic data within a host-specific context (i.e., a prognostic determinant).

The clinical validity of any proposed genomic test rests on how well the polymorphism predicts the trait of interest. Oftentimes the gene is expressed in an inaccessible tissue (i.e. the nervous system or heart muscle) and only proxy phenotypic data is available to researchers and clinicians. To the contrary, in the present circumstance the $P2X_7$ receptor is expressed within circulating elements of the blood readily available from all patients. In the future, therefore, the invention provides the capacity to correlate raw clinical data with genomic and pore assay results to sharply refine corollary diagnostic and management pathways of optimal benefit to individual patients.

Therefore, the present invention in one embodiment provides a rapid method of assaying nucleotide receptor $P2X_7$ pore activity in white blood cells. The method is particularly suited for practice in the clinical setting and includes the steps of: (a) labeling white blood cells with a white blood cell-specific label; (b) depolarizing the labeled white blood cells in an isotonic depolarizing solution; (c) contacting the labeled white blood cells with a dye and a $P2X_7$ agonist in an amount sufficient to activate nucleotide receptor $P2X_7$ pore activity;

(d) contacting the labeled white blood cells of step (c) with a divalent cation in an amount sufficient to deactivate nucleotide receptor $P2X_7$ pore activity; and (e) analyzing dye uptake in labeled white blood cells of step (d) whereby nucleotide receptor $P2X_7$ pore activity is quantified by the amount of dye taken up in labeled white blood cells treated with the $P2X_7$ agonist relative to labeled white blood cells in the absence of the $P2X_7$ agonist.

In a preferred embodiment, the white blood cell label is an antibody directed against surface antigen CD14. Because $P2X_7$ is expressed on all white blood cells, it is conceivable that any leukocyte cell surface protein could be labeled with an antibody or equivalent white blood cell-specific reagent. For detection purposes to be described below, a fluorescent conjugate to the antibody is utilized. A preferred fluorescent conjugate is phycoerythrin. An essential feature of the invention is that the conjugate must be bright enough such that the labeled cells can be resolved against the background contributed by the unlabeled cells. Without this separation, the signal from the labeled cells becomes lost in the noise contributed from the overwhelming number of red blood cells and platelets, which are in excess by a factor of 1,000 to 100,000 in whole blood samples.

The compound 2'-3'-O-(4-benzoylbenzoyl)-adenosine 5'-triphosphate, called Bz-ATP, is a preferred $P2X_7$ agonist because it is the most potent and efficacious $P2X_7$ agonist known. Others include, but are not limited to, adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5'(beta,gamma-imido)triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof. Because pore activity is a relatively unique property of $P2X_7$ function, other agonists could be used, not named herein, provided that they are able to facilitate pore formation.

$P2X_7$ is a nonselective cation channel that allows agonist-dependent passage of sodium, potassium and calcium. After brief stimulations ($\leq 1$ sec), removal of the agonist is associated with cessation of these nonselective currents with minimal desensitization, such that repetitive, brief agonist applications do not attenuate the maximum achievable current amplitude. Longer applications of agonist allow passage of cations with progressively larger diameters. The pattern of time constants associated with the passage of increasingly large cations is not consistent with a model of simple diffusion, suggesting that the channel diameter dilates with chronic administration of agonist. "Pore activity" is defined as the passage of larger molecules, including fluorescent dyes, with an upper mass limit of approximately 900 daltons. The process associated with pore dilation requires at least a few seconds of agonist administration, is reversible upon agonist removal, and is modulated by temperature, as well as the concentrations of sodium, chloride and divalent cations in the extracellular solution.

In order to maximize the signal obtained from the white blood cells of an individual with two normal copies of the $P2X_7$ gene, the pore assay includes a unique and previously undescribed step in which an isotonic depolarizing solution is contacted with the labeled white blood cells. The isotonic depolarizing solution utilized herein is a solution lacking sodium and chloride ions and divalent cations in amounts effective to inhibit $P2X_7$ pore activity. This reagent is preferably a solution comprising glutamate ion (e.g., a potassium glutamate buffer). This novel step provides a greater separation of the signal obtained from wild type individuals compared to those with mutations. The unique feature here is the absence of extracellular sodium, and to a lesser extent, chloride because these ions inhibit pore activity. Facilitation of pore activity is further done in the absence of divalent cations that also inhibit pore activity.

Because dilation of the pore allows for passage of large molecules with masses of <900 daltons, fluorescent dyes of several varieties and specificities may be used provided that they can fit through the pore. YO-PRO-1 is a preferred macromolecule DNA-binding dye because when activated it has a very intense signal. The key feature here is that the dye must provide a signal brighter than the background contributed by the antibody-labeled white cells in the presence of the dye, but the absence of the $P2X_7$ agonist. The dye preferably provides a signal at least ten times brighter than the background contributed by the antibody-labeled white cells in the presence of the dye but the absence of the $P2X_7$ agonist.

In a preferred embodiment, magnesium ion, preferably provided as a $MgCl_2$ solution, is added at a defined time in an assay according to the invention to close the pore, and add precision and the ability to automate the assay. This step is not contemplated by previous methods of assaying $P2X_7$ pore activity but provides a significant technical advantage in the present methods. Other divalent cations may also be used, provided that they do not induce clotting of the solutions containing whole blood.

In a preferred embodiment, dye uptake in step (e) is measured by flow cytometry. Flow cytometry detects labeled white blood cells apart from non-labeled cells and measures intensity of the dye taken up by the labeled white blood cells whereby nucleotide receptor $P2X_7$ pore activity is quantified by the amount of dye taken up in labeled white blood cells treated with the $P2X_7$ agonist relative to labeled white blood cells in the absence of said $P2X_7$ agonist.

The preferred flow cytometry parameters will now be described. Cells from whole blood (i.e., red/white blood cells and platelets) are analyzed on a flow cytometer (available from Becton Dickinson, San Jose, Calif., under the trade name FACSca) calibrated daily using standard fluorimetric beads. The instrument settings were derived using purified blood monocytes that had been separated from the red cells and stained with a phycoerythin-conjugated anti-CD14 antibody in the presence and absence of YO-PRO. The intensity of the YO-PRO signal creates a significant amount of spectral overlap into the phycoerythrin detector. This overlap is electronically subtracted so that phycoerythrin negative events that incorporate YO-PRO can be conveniently distinguished from positively labeled white blood cells. The phycoerythrin signal is collected with a 585 nm filter with a 42 nm band pass, whereas the YO-PRO signal is collected with a 530 m filter and a 30 nm band pass. Using the results from the purified monocytes, the instrument is then adjusted to trigger on the phycoerythrin signal by setting the threshold above the background associated from unlabeled cells. Thus, data from all non-phycoerythrin labeled cells are omitted. Because the YO-PRO signal is intense, channel compensation is used to eliminate the YO-PRO signal in the phycoerythrin channel.

For each experiment with whole blood, the standard instrument settings are called up from a stored file and used without adjustment. To correct for any slight variation in the flow cytometer's performance, fluorescent standard beads may be analyzed as is standard technique in the field. To reduce viscosity, the whole blood is diluted 1:4 in a standard saline solution. Ten thousand phycoerthrin-labeled events are acquired using CellQuest acquisition and analysis software (Becton Dickinson) and the amount of YO-PRO taken up by these cells is measured in the presence or absence of prior stimulation with the $P2X_7$ agonist, Bz-ATP.

The present invention is also a method of assaying nucleotide receptor $P2X_7$ pore activity in a blood sample including white blood cells, comprising the steps of: (a) labeling white blood cells included within the blood sample with a white blood cell-specific label; (b) depolarizing the labeled white blood cells in an isotonic depolarizing solution; (c) contacting the labeled white blood cells with a $P2X_7$ agonist in an amount sufficient to activate nucleotide receptor $P2X_7$ pore activity and a dye; (d) contacting the labeled white blood cells of step (c) with a divalent cation in an amount sufficient to deactivate nucleotide receptor $P2X_7$ pore activity; and (e) analyzing dye uptake in labeled white blood cells of step (d) whereby nucleotide receptor $P2X_7$ pore activity is quantified by the amount of dye taken up in labeled white blood cells treated with the $P2X_7$ agonist relative to labeled white blood cells in the absence of said $P2X_7$ agonist.

Figure 6:
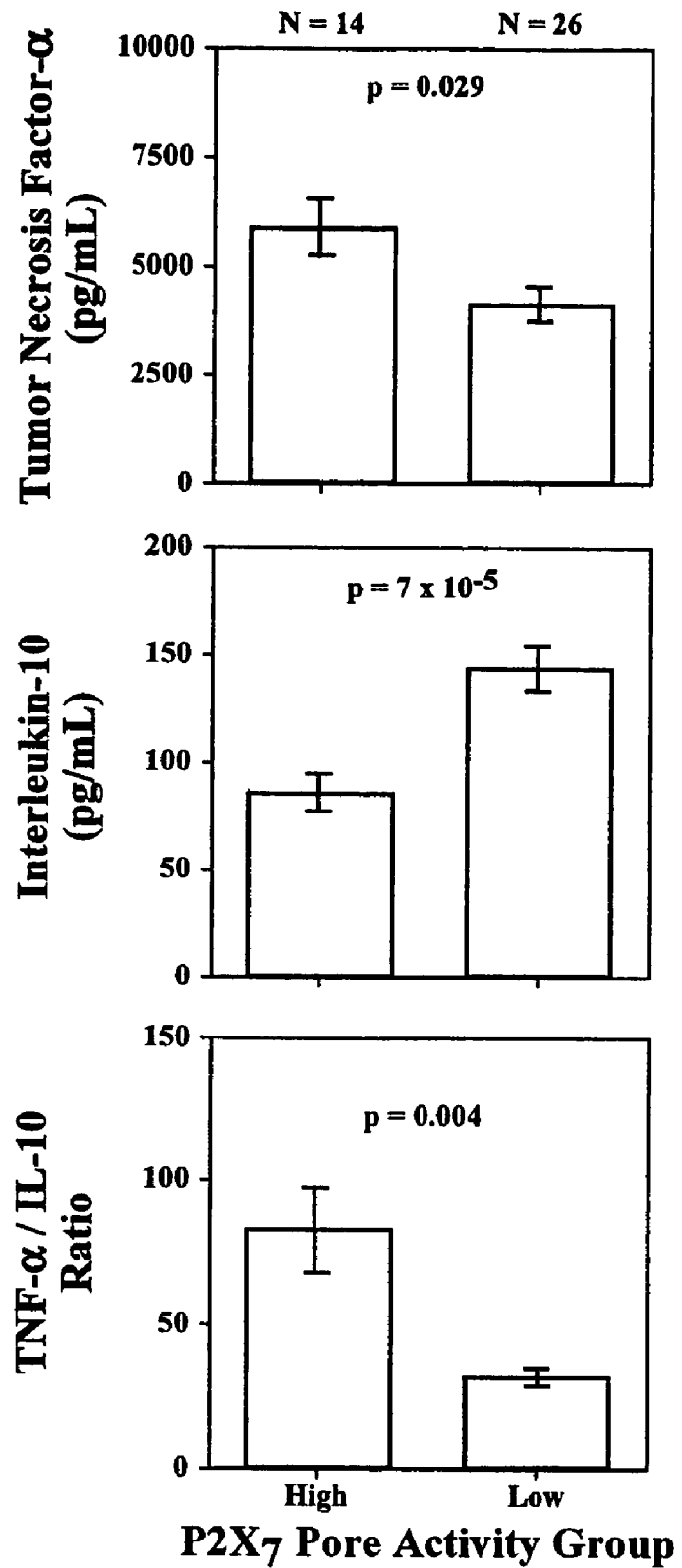
FIG. 6 shows LPS-stimulated whole blood production of tumor necrosis factor-α and interleukin-10. Whole blood samples from Phase II subjects were stimulated for 6 hr at 37° C. with 0 or 100 ng/mL of *Salmonella typhimurium* LPS followed by centrifugation to harvest plasma. The control samples contained undetectable levels of these cytokines. Data shown are the group means and standard errors from fourteen and twenty-six subjects per group (high vs. low pore activity). The results are representative of two experiments seen using a sandwich ELISA and a cytokine array from Pierce Biotechnology, Inc. under the trademark SEARCHLIGHT. The TNF-α to IL-10 ratio was calculated on an individual subject basis prior to deriving group means and standard errors. Results from unpaired Student's t-tests with adjustment for unequal variance are also shown.

Because of the well-known links between monocyte $P2X_7$ pore activity and IL-1 beta processing, the identification of deficient pore activity will correlate with lowered plasma levels of IL-1beta. This has recently been demonstrated at early time points (Sluyter et al. J. Immunol. 172:3399-3405 (2004). Additionally, the present inventors have recently shown that subjects with low $P2X_7$ pore activity relative to wild type controls have a reduced TNF-alpha to interleukein-10 ratio in response to LPS-treatment of whole blood (FIG. 6). The capacity to quickly ascertain this information, particularly in the clinical setting, allows medical practitioners to predict a particular subject's susceptibility to, for example, sepsis or septic shock and response to varied courses of treatment. Prior $P2X_7$ pore assay techniques did not allow this abbreviated turn around time from sample collection to results, so crucial to patient care in the fast-paced clinical setting. It should be noted that sepsis is only one particular area where molecular phenotype data regarding the $P2X_7$ pore activity is useful as a prognostic determinant, as will be further explored below.

Therefore, in yet another embodiment, the invention provides a method of identifying a nucleotide receptor $P2X_7$-related molecular phenotype useful as a prognostic determinant of a clinical outcome in a patient, comprising the steps of: (a) carrying out a pore assay according to the invention on white blood cell samples from a patient population having known clinical outcomes to determine a plurality of receptor $P2X_7$ pore activities; and (b) correlating the nucleotide receptor $P2X_7$ pore activities with the known clinical outcomes to determine statistically significant correlations between respective pore activities and known clinical outcomes thereby determining a particular nucleotide receptor $P2X_7$ molecular phenotype useful as a prognostic determinant in a patient.

A wide variety of clinical studies are made possible by rapid pore assays according to the present invention. For example, patients who develop septic shock may be examined using the present invention to determine if they have a different $P2X_7$ A1513C allele distribution than intensive care unit (ICU) control patients, and consequently whether this is a major predictor of variance in endogenous cytokine profiles. This study will identify $P2X_7$ genotype frequencies in patients with septic shock relative to ICU control patients and correlate these frequencies with the cytokine profile detected from unstimulated (ex vivo) whole blood by techniques known in the art. With these endpoints and estimated frequencies from the current data set in healthy subjects, a sample size of 150 patients in each group will provide sufficient statistical power to detect significant differences. Other variables to be included in the regression models would be confounding SNPs at other loci (e.g. the LPS receptor system, CD14/TLR4) and clinical parameters (comorbid conditions, source of infection, class of organism, etc). Adjustments for multiple comparisons would be taken into account up front to help limit the number of parameters entered into the regression models. An expanded version of this trial could be coupled with a multi-center trial of an intervention protocol vs. standard of care, enrolling 500 or more septic patients. The hypothesis in this case is that patients with low $P2X_7$ pore activity conferred by the $P2X_7$ 1513 C/C genotype or other genotypes who develop septic shock have a worse prognosis with respect to length of stay in the ICU and/or mortality. Similar considerations for regression modeling as discussed above would also pertain to this trial.

Finally, because the surface expression and pore activity of $P2X_7$ in monocytes may depend upon the C-terminal lipid interaction motif that binds LPS, the whole blood pore assay may be an early predictor of bacteremia in patients with an infection, and subsequent progression to septic shock, and thereby serve as a prognostic determinant. A clinical study aimed at developing this concept would directly utilize information obtained from the $P2X_7$ structure/function analysis. As an example, the current protocol for the pore assay described above with results depicted in, for example, FIG. 4 is intentionally designed to be highly sensitive in the detection of C/C mutants, at the expense of being less specific for subjects with the A/C or A/A genotypes. Using different agonist and buffer systems, the capacity to open the pore in monocytes can be dampened significantly, such that a normal response even with the A/A genotype is quite diminished. These conditions might make it possible to detect monocytes from bacteremic patients that have greater surface localization of $P2X_7$ and hence supranormal levels of pore activity. The two sets of assay conditions could be used in parallel such that there is discrimination between current patient physiology and total capacity for monocyte pore formation. The targeted potential patient population for study in this case would be noncritical hospital patients with infections, as a way to identify those with increase risk of becoming septic. As early diagnosis and implementation of supportive therapy for patients with septic shock has been shown to improve patient outcomes (3), this type of rapid diagnostic test has the potential to serve as the ultimate translation of bench research.

Rapid assays according to the present invention will thusly be used to, for example, identify more specific ways to prospectively stratify patients with severe sepsis and septic shock by understanding the genetic and molecular contributions of the nucleotide receptor $P2X_7$ on monocyte and macrophage functionality (i.e., the identification of prognostic determinants). In addition to sepsis-related studies, the present invention will be useful in the ex vivo analysis of $P2X_7$ pore activity in regard to other problematic infections including those infections caused by or related to, for example, *Staphylococcus aureus*, *Pseudomonas aeruginosa* and *Blastomyces* (i.e. the effect of organisms lacking endotoxin on pore activity and cytokine profiles).

The use of the present invention for screening the variability in $P2X_7$ function is also envisioned to allow the rapid and convenient collection of preliminary data for potential patient populations such as those suffering from tuberculosis, asthma, pneumonia, urosepsis, rheumatoid arthritis, lupus, Crohn's Disease, ulcerous colitis, parasitic infections (e.g., leishmaniasis), transplant rejection or chronic lymphocytic leukemia (CLL), acute or chronic forms of axonal injury and neurodegenerative disorders. Regarding CLL, Wiley et al.

(see Lancet 359, 1114-1119 (2001)) reported that the frequency of the non-functional 1513C allele was greater in a series of patients with indolent CLL than in normal individuals. They also studied the occurrence of the 1513A to C polymorphism in two pedigrees with familial CLL, and found affected members of these families to be either heterozygous or homozygous for the 1513C allele. Wiley et al suggested that loss of $P2X_7$ function produced an antiapoptotic effect and contributed, along with the overexpression of the BCL2 gene, to the accumulation of leukaemic B cells in the circulation. They also suggested that genetic haploinsufficiency of $P2X_7$ might contribute to the well-recognized familial incidence of CLL. As can be appreciated by one of skill in the art, a rapid pore assay would provide an additional clinical tool in diagnosing patients suffering from CLL or with a predisposition to CLL.

With respect to an infectious process, Lammas and colleagues found that the C allele of a $P2X_7$-762 promoter polymorphism was associated with a lower incidence of smear-positive pulmonary tuberculosis in a Gambian population (Li et al. 2002 J Infect Dis 186:1458-62). Although neither this nor four other promoter polymorphisms appear to affect surface $P2X_7$ expression (Li et al. 2002 FEBS Lett 531:127-31) this receptor has been shown to have a large intracellular pool that promotes phagolysosomal maturation needed to facilitate killing of *Mycobacteria tuberculosis* (Fairbaim et al. 2001. J. Immunol. 167:3300-7, and Lammas et al. 1997 Immunity 7:433-44). Thus, if the −762 C allele is associated with enhanced mRNA and/or protein trafficking, these individuals may be better able to clear the initial infection such that they do not progress to active disease. In addition, individuals with the $P2X_7$ 1513 CC genotype have monocytes that are less able to kill the BCG strain of *M tuberculosis* (Saunders et al. 2003 *J. Immunol.* 171:5442-6). Thus, individuals with loss-of-function $P2X_7$ alleles may also be at risk for a worse outcome in the setting of certain types of infection, such as those from intracellular pathogens.

In light of the above, the pore assay provided herein will be integral in the identification and correlation of $P2X_7$ pore activities and underlying-alleles with clinical outcomes so that reliable prognostic determinants may be identified. Such prognostic determinants will provide the knowledge to allow refining of immunomodulatory or immunosuppressive as well as anti-infectious therapy on a patient-by-patient basis. Thus, a further embodiment of the invention is directed to a method of identifying a nucleotide receptor $P2X_7$-related polymorphism useful as a prognostic determinant of a clinical outcome in a patient, comprising the steps of: (a) carrying out a pore assay according to the invention on white blood cell samples from a patient population having known clinical outcomes to determine a plurality of respective receptor $P2X_7$ pore activities; (b) correlating the nucleotide receptor $P2X_7$ pore activities with the known clinical outcomes to determine statistically significant correlations between respective pore activities and known clinical outcomes; and (c) characterizing genomic material from respective patients in which statistically significant correlations were identified in step (b) to identify a nucleotide receptor $P2X_7$-related polymorphism useful as a prognostic determinant.

It is envisioned that $P2X_7$ gene polymorphisms, identified through application of the present invention, may be collected to create a database upon which future medical detection techniques will be based. For example, $P2X_7$ gene polymorphisms in an individual patient may be rapidly assayed in the future by the preparation and use of DNA microarray assays. In general, such assays utilize a series of oligonucleotide or cDNA probes affixed to a solid support. The probes are designed to be unique to a given SNP or mutation. The DNA template of interest is then contacted with the DNA microarray and $P2X_7$ hybridization is detected. In one embodiment, such assays will utilize gene "chip" substrates having affixed probe nucleic acids (e.g., oligonucleotides or cDNAs) representing $P2X_7$ gene polymorphisms from an above-described database. A nucleic acid sample from the patient may be incubated with the gene chip substrate under conditions favorable for the specific hybridization of the sample nucleic acids with their complementary probe sequences affixed to the gene chip substrate. After incubation, all non-hybridized sample nucleic acids are removed from the sample nucleic acid:probe hybrid. The presence of nucleic acids which have hybridized, if any such molecules exist, is then detected using standard techniques well-known to those in the art. The probe gene sequence(s) to which the sample nucleic acids have hybridized can be compared to the hybridization pattern expected from a wild type $P2X_7$ gene sequence in order to determine whether a $P2X_7$ gene polymorphism is present. Based upon known correlations between $P2X_7$ gene polymorphisms and clinical outcome, medical practitioners may then be directed to a patient-specific clinical pathway. Microarray technologies amendable for accessing $P2X_7$ gene polymorphisms include, but are not limited to, the inventions disclosed in: U.S. Pat. No. 5,837,832 to Chee et al., assigned to Affymetrix, Inc.; U.S. Pat. No. 5,837,832 to Nerenberg et al., assigned to Nanogen, Inc.; and U.S. Pat. No. 6,355,431 to Chee et al., assigned to Illumina, Inc. Other technologies understood in the art to facilitate polymorphism detection are also amendable for use in such approaches and include, for example, the proprietary platform available from Third Wave Technologies, Inc., under the federally-registered trademark INVADER.

The invention also encompasses a method of providing immunosuppressive and anti-infectious therapy to a patient, comprising the steps of: (a) analyzing a white blood sample from the patient by a pore assay as described herein to obtain a nucleotide receptor $P2X_7$ pore activity for the patient; and (b) comparing the nucleotide receptor $P2X_7$ pore activity with previously-determined nucleotide receptor $P2X_7$ pore activities that demonstrate statistically significant correlation to clinical outcomes; and (c) based upon the result of step (b), providing therapy to either avoid or achieve a particular clinical outcome in the respective patient.

In still another embodiment, this invention provides kits for practice of the methods described herein. The kits will include instructions and, optionally, any reagents and/or apparatus to facilitate practice of the methods. For example, a kit may include buffer solutions, positive and/or negative controls, or calibration standards. In one preferred embodiment, the kits comprise operational instructions and one or more containers containing the necessary stock or working solutions to carry out the present invention. Kits may be directed to determining a molecular phenotype (i.e., pore activity) or a genotype (e.g., a known or unknown SNP).

The kits will include instructional materials containing directions (i.e., protocols) for the functional use of the kit, and, optionally, for interpretation of test results. Preferred instructional materials provide protocols utilizing the kit contents for measuring $P2X_7$ pore activity in a blood sample. Any medium capable of storing instructional materials and communicating them to an end user is contemplated by this invention. Such media include, but are not limited to printed media, electronic storage media (e.g., magnetic discs, tapes, cartridges, chips), optical media (e.g., CD ROM), and the like. Such media may include addresses to internet sites that provide such instructional materials. In addition, certain kit embodiments may contain algorithms or decision trees pointing to subject-specific clinical pathways (i.e., best practices) based on kit-facilitated test results. For example, if in a subject with clinical presentation X, and genotype Y, pore assay result Z is observed, then clinical pathway I is recommended. Conversely, if in a subject with clinical presentation A, and genotype B, pore assay result C is observed, then clinical pathway II is recommended. These examples set forth the manner in which instructions provided in a kit according to the invention may guide the construction of patient specific algorithms that cannot be traversed in advance of obtaining a pore assay result.

As described herein, the steps of preparing a plurality of pore assays according to the invention include an appreciable number of iterative steps where large sample numbers are to be processed, as would be anticipated in the clinical setting. The invention's lack of complex purification steps and unique manipulation of pore activity by specific reagents (e.g., divalent cation added to halt pore activity) make the present methods especially well suited to automation of one or more of each of its steps. It is therefore envisioned that the invention may be performed by any automated means including those containing a computer-readable medium carrying a sequence of instructions, where executing the sequence by a processor causes the processor to direct the steps of the method. An example of an automated means suitable for automating one or more of the present invention's steps is disclosed in U.S. Pat. No. 6,326,147 to Oldham et al.

It is further envisioned that the present invention may be carried out in a micro-titer plate format. In an embodiment based thereon, wells within a micro-titer plate would be coated with, for example, anti-CD14 antibodies. In a single well, whole blood, an isotonic depolarizing buffer, dye and +/− agonist would be mixed followed after a time period by addition of a divalent cation. Following a washing step which would eliminate cell types not bound by the anti-CD14 antibodies (e.g., red blood cells and platelets), dye uptake would be quantified by a fluorimetric plate reader to determine a $P2X_7$ pore activity.

The inventors estimate a pore assay according to the invention (e.g., as described in Example 1 below) may be manually carried out in as little as two hours from blood collection to data analysis, drastically less than the analysis intervals required by previous techniques, and automation may further minimize the necessary time involved.

As well, one of skill in the art, after consideration of the invention described herein, will be able to adapt through minimal routine experimentation the present invention for assay of pore activity in a wide variety of channel proteins. Such channels include both $P2X_7$-related channels (i.e., channels in the purinoreceptor family, particularly the P2X subgroup) and channels unrelated in homology to the P2X channels but characterized by similar ionotropic behavior. In addition, the methodology described herein is also amendable for assaying pore activity in cell types other than white blood cells by no more than routine selection of cell-specific label, agonist/antagonist, dye and optimization of flow cytometry parameters based upon the present disclosure.

The following Examples are offered by way of illustration and not by way of limitation.

III. EXAMPLES

Example 1

This example sets forth a preferred method for rapid measurement of monocyte $P2X_7$ pore activity by flow cytometry of washed whole blood.

Aliquots of citrated whole blood (500 μL/aliquot) were washed twice in HEPES-buffered saline (HBS; 130 mM NaCl, 5 mM KCl, 20 mM HEPES pH 7.4, 0.1% bovine serum albumin, 10 mM glucose; components purchased at Sigma, St. Louis, Mo.) and then labeled at room temperature with 125 ng of an anti-human CD14 antibody conjugated to phycoerythrin (BD Biosciences, San Diego, Calif.). After twenty minutes, the cells were washed twice in a potassium glutamate buffer (130 mM potassium glutamate, 5 mM KCl, 20 mM HEPES pH 7.4, 0.1% bovine serum albumin, 10 mM glucose; components from Sigma) to maximize the differences between high and low pore activities (18). In the absence of NaCl, cells were stimulated for twenty minutes with 0 or 250 μM 2'-3'-O-(4-Benzoylbenzoyl) adenosine 5'-triphosphate (Bz-ATP; Sigma) in the presence of 1 μM YO-PRO-1 (Molecular Probes, Eugene, Oreg.). Samples were then adjusted to 10 mM magnesium chloride, washed in HEPES-buffered saline and diluted to a volume of 2.5 mL in HBS.

Flow cytometry was performed on a flow cytometer (Becton Dickinson, San Jose, Calif., under the trade name FACSca) that is calibrated daily using standard fluorimetric beads. The instrument settings were derived prior to enrolling study subjects using purified blood monocytes that had been separated from the red cells with Ficoll-Hypaque (Sigma), and stained with a phycoerythrin-conjugated anti-CD14 antibody in the presence and absence of YO-PRO-1. The phycoerythrin signal was collected with a 585 nm filter with a 42 m band pass, whereas the YO-PRO-1 signal was collected with a 530 nm filter and a 30 nm band pass. Using the results from the purified monocytes, the instrument was then set to trigger on the phycoerythrin signal by setting the threshold above the background associated from unlabeled cells. Thus, data from all non-phycoerythrin labeled cells were not acquired. Because the YO-PRO-1 signal is so intense, channel compensation (approximately 30%) was used to eliminate the YO-PRO-1 signal in the phycoerythrin channel.

For each experiment with washed whole blood from the study subjects, the standard instrument settings were called up from a stored file and used without adjustment. Ten thousand phycoerthrin-labeled events were acquired using CellQuest and CellQuestPro acquisition and analysis software (v. 3.3 and 4.0; Becton Dickinson) and the amount of YO-PRO-1 taken up by these cells was measured in the presence or absence of prior stimulation with the $P2X_7$ agonist, Bz-ATP. Data analysis was done as a batch using FlowJo software (v. 4.3; Tree Star, Inc., Palo Alto, Calif.) in order to apply the same CD14+ gates to the entire study. The fold stimulation of $P2X_7$ pore activity was calculated using the ratio of the geometric mean of YO-PRO-1 fluorescence associated with the Bz-ATP-treated sample relative to that derived from the control.

Previous methods used to study the $P2X_7$ pore activity in primary cells include the lysis of erythrocytes, the isolation of whole blood leukocytes by gradient centrifugation or the purification of lymph node T cells (19,27). Because the inventors were interested in identifying individuals with novel $P2X_7$ genetic polymorphisms, they developed an assay that is more amenable to larger screens, potentially with greater sensitivity for detecting alleles with subtle influence on leukocyte P2X$_7$ pore activity. As shown in FIGS. 1A and 1B, the ability to detect specific populations of leukocytes according to their size and granularity was lost in the context of whole blood due to noise created by an overwhelming number of erythrocytes and platelets. However, labeling these cells with a CD14 specific antibody allowed for the use of a threshold technique to rapidly identify monocytes in whole blood samples (FIG. 1, panels C and D).

Figure 2:
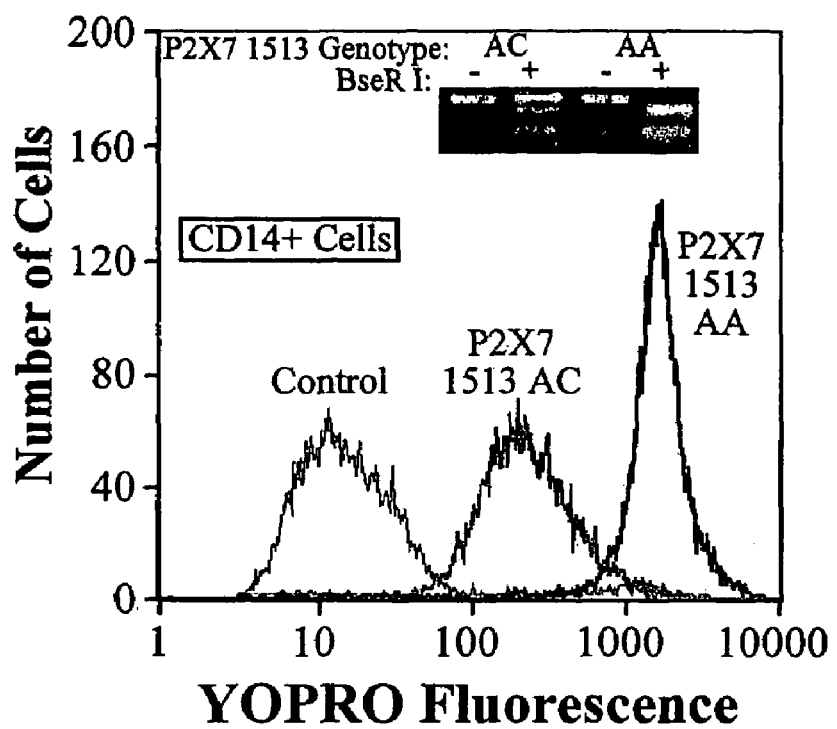
FIG. 2 displays representative pore assay data from three subjects with different $P2X_7$ A1513C genotypes. Histogram representations are shown separated horizontally according to the amount of YO-PRO-1 taken up by CD14+ cells stimulated with 250 µM Bz-ATP or the saline control. Panel A shows data from the one individual each with the common 1513 AA and heterozygous AC genotypes, whereas Panel B contains data from one subject with the uncommon CC genotype. Inset panels are the corresponding data from the PCR product restriction fragment length polymorphism analysis with the endonuclease BseRI.
Figure 2:
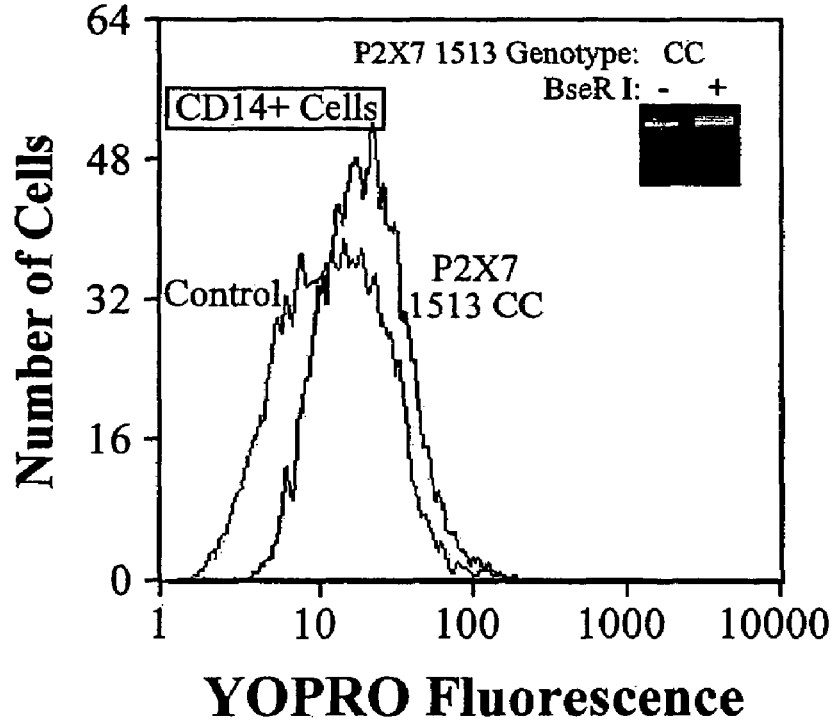
Figure 3:
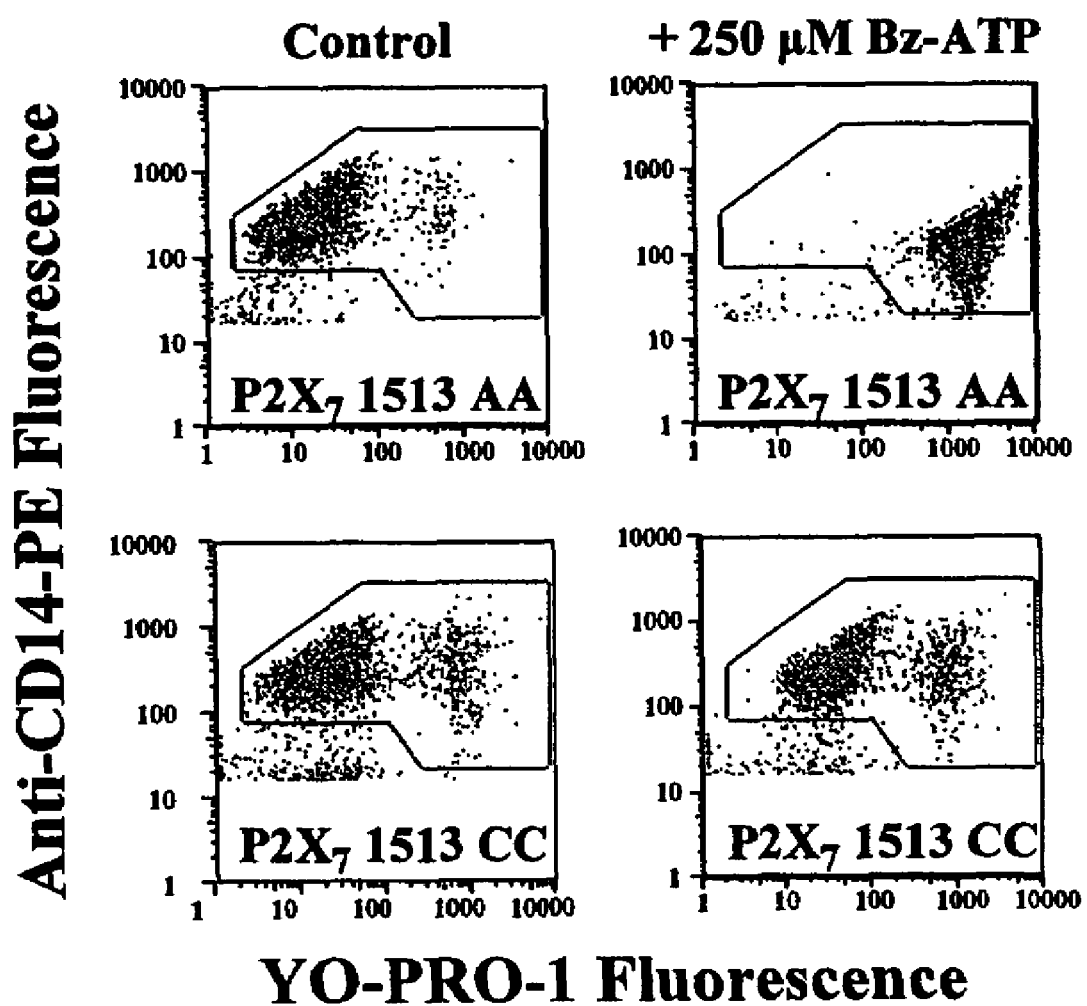
FIG. 3 depicts monocyte $P2X_7$ pore activity as measured by Bz-ATP-stimulated uptake of YO-PRO-1 in whole blood. Anti-CD14 antibody-labeled whole blood is treated with zero or 250 µM Bz-ATP for 20 minutes in the absence of sodium chloride at room temperature, followed by pore closure with 10 mM $MgCl_2$. Uniform flow cytometer settings and gates were used throughout the study. Data from CD14-negative cells are not acquired, allowing for the collection of 10,000 $CD14^+$ events. The figure shows data from one subject each with the $P2X_7$ 1513 common AA and variant CC genotypes.

By choosing conditions that amplify pore activity, this whole blood assay produced large differences between the monocyte pore activity in samples from individuals with the P2X$_7$ 1513 CC genotype relative to those from subjects with the AC or AA genotypes (FIG. 2). Specifically, treatment of washed whole blood for twenty min with the potent P2X$_7$ agonist Bz-ATP in an isotonic buffer solution lacking sodium chloride allowed for the passage of the fluorescent dye YO-PRO-1 (FIG. 2). This assay produced a stable phenotype in that the range of day-to-day variability from forty-one subjects averaged at 31±22% of the individual subject's mean.

Further referring to the data shown in FIG. 2, genomic DNA was prepared from frozen whole blood samples using the Puregene DNA Isolation kit (Gentra Systems, Minneapolis, Minn.). Genotypes were determined by PCR-based restriction fragment length polymorphism analysis and sequencing, as described in the following example 2. In the inset panels, products from the polymerase chain reaction using P2X$_7$-specific primers and genomic DNA were treated with and without the restriction endonuclease BseRI and then separated by agarose gel electophoresis and visualized by staining with ethidium bromide using standard techniques known in the art. The main panels illustrates data provided by the present invention and show Bz-ATP-induced uptake of the fluorescent dye YOPRO by cells in whole blood stained with an antibody to the cell surface maker CD14, as detected by flow cytometry. Control CD14 labeled cells in the absence of P2X$_7$ agonist display a dye uptake shifted left on the x-axis (i.e., lower dye intensity indicated less dye uptake thus lower P2X$_7$ pore activity in the assayed cells). The C/C, A/C and A/A genotypes can be easily distinguished from each other. Note that in FIG. 2A, the A/C genotype having a dye uptake intermediate between control cells and A/A cells treated with agonist. Thus, the assay described and claimed herein has the capacity to distinguish between P2X$_7$ genotypes, namely, 1513 C/C homozygous individuals, 1513 A/C heterozygous individuals and 1513 A/A homozygous individuals.

Studies described in this example relating to humans were performed in accordance with the principles of the Declaration of Helsinki, and was prospectively approved by the University of Wisconsin Institutional Review Board. Furthermore, all participating subjects verified their informed consent in writing.

Example 2

This example describes how the detection of human P2X$_7$ nucleotide receptor polymorphisms by a pore assay according to the invention is predictive of alterations in LPS-induced cytokine production.

As described in previous sections, the nucleotide receptor P2X$_7$ is expressed by most classes of leukocytes and initiates signaling events that act as an amplification loop for numerous LPS responses. The inventors tested the hypothesis that loss-of-function polymorphisms in the human P2X$_7$ gene predispose to the production of an anti-inflammatory mediator balance. Accordingly, the inventors developed a novel P2X$_7$ pore assay in whole blood that magnifies the activity from wild type alleles and preserves the gene dosage effect for the 1513 C polymorphism (AA, 69±4; AC, 42±4; and CC, 6±1-fold stimulation). Thirty of two hundred healthy individuals were identified as having low P2X$_7$ pore activity. Because platelets are a large source of extracellular ATP during inflammation, whole blood was treated ex vivo with *Salmonella typhimurium* LPS in the absence of exogenous nucleotides. Individuals from the low pore activity group generated reduced plasma levels of tumor necrosis factor-α (p=0.029) and higher amounts of interleukin-10 (p=7×10-5). The ability of P2X$_7$ polymorphisms to regulate the LPS-induced TNF-α to IL-10 ratio suggests that 15% of healthy adults may exhibit anti-inflammatory mediator responses during major infectious perturbations of the immune system, which can be predicted by P2X$_7$ pore activity.

Materials and Methods

Human subject participation. Investigations were carried out with approval of the University of Wisconsin Institutional Review Board, and written informed consent was obtained from all the participants. Two hundred healthy (paid) volunteers between the ages of 18 and 50 were enrolled for the first phase of the study on thirty-five days over the course of a year with one to nine subjects enrolled per study-day. None had been hospitalized in the last year or used medicines on a daily basis. Ten mL of whole blood were obtained by routine phlebotomy from each participant, assigned an anonymized code number, and anticoagulated with EDTA or citrate respectively for genetic and flow cytometric experiments.

Forty of these initial two hundred subjects were recruited for a second, cytokine phase of the study. In this phase, all seven subjects with the P2X$_7$ 1513 CC genotype and low monocyte pore activity were enrolled, together with fourteen randomly selected subjects from both the 1513 AA and AC groups (7 per group) with high (i.e. normal) pore activity. As discussed below in the Results section, twenty-three phase I subjects exhibited low pore activity despite P2X$_7$ 1513 common AA or heterozygote AC genotypes. Of this latter group, nineteen subjects were enrolled with four lost to follow up. Enrollment for the forty subjects in the second phase was done on seven different days with three to seven subjects per day, and the investigators were blind to the scheduling details of any individual subject. Fifteen mL of whole blood were obtained from each participant at the return visit in either EDTA or citrate tubes for genetic, flow cytometric, and cytokine experiments. A second anonymized code was assigned to these samples such that the investigators performing the cytokine experiments were blind to the genetic and flow cytometry results.

Determination of the P2X$_7$ A1513C and T1729A genotypes. Genomic DNA was prepared from frozen whole blood samples using the Puregene DNA Isolation kit (Gentra Systems, Minneapolis, Minn.). Polymerase chain reaction (PCR) primers for exon 13 of the human P2X$_7$ gene were identical to those described by Gu et al (19) (which amplifies a 356 bp product sufficient to incorporate both the 1513 and 1729 loci), and were synthesized by Integrated DNA Technologies (Coralville, Iowa). The final concentration of magnesium chloride was 1.5 mM and the annealing temperature was 58° C. The PCR product was digested with 2 units of the restriction endonuclease BseRI overnight at 37° C. The fragments were separated by gel electrophoresis in 1.5% agarose and observed by ethidium bromide staining. The P2X$_7$ 1513 C allele disrupts the BseRI palindromic sequence, thus the corresponding PCR fragment is not digested producing three bands for the 1513 AC genotype (356, 256, and 100 bp) and one band for the CC individuals (356 bp). Because the latter result cannot be discerned from the uncut fragment, PCR products from subjects with the 1513 CC genotype were sequenced bi-directionally (UW Biotech Center). Additionally, the PCR product from P2X$_7$ exon 13 was sequenced for all subjects enrolled in the cytokine phase of the protocol to determine the T1729A genotype.

Monocyte P2X$_7$ pore activity measured by flow cytometry of washed whole blood. Monocytes were selected as the cell population to screen because of the greater variability in pore function noted between individuals participating in a small study with 45 healthy subjects (19). Aliquots of citrated whole blood (500 μL/aliquot) were washed twice in HEPES-buffered saline (HBS; 130 mM NaCl, 5 mM KCl, 20 mM HEPES pH 7.4, 0.1% bovine serum albumin, 10 mM glucose; components purchased at Sigma, St. Louis, Mo.) and labeled at room temperature with 125 ng of an anti-human CD14 antibody conjugated to phycoerythrin (BD Biosciences, San Diego, Calif.). After twenty minutes, the cells were washed twice in a potassium glutamate buffer (130 mM potassium glutamate, 5 mM KCl, 20 mM HEPES pH 7.4, 0.1% bovine serum albumin, 10 mM glucose; components from Sigma) to maximize the differences between high and low pore activities (18). In the absence of NaCl, cells were stimulated for twenty minutes with 0 or 250 μM 2'-3'-O-(4-Benzoylbenzoyl) adenosine 5'-triphosphate (Bz-ATP; Sigma) in the presence of 1 μM YO-PRO-1 (Molecular Probes, Eugene, Oreg.). Samples were then adjusted to 10 mM magnesium chloride, washed in HEPES-buffered saline and diluted to a volume of 2.5 mL in HBS.

Flow cytometry was performed on a FACScan flow cytometer (Becton Dickinson, San Jose, Calif.) calibrated daily using standard fluorimetric beads in conjunction with the CellQuest and CellQuestPro acquisition and analysis software (v. 3.3 and 4.0; Becton Dickinson). Instrument settings (forward scatter, E00 mV; side scatter, 458 mV; FL-1, 410 mV; FL-2, 412 mV; acquisition threshold for FL-2, 324 mV; compensation, FL-2-32.6% FL-1) were derived prior to enrolling study subjects using purified blood monocytes that had been separated from the red cells with Ficoll-Hypaque (Sigma), and stained with a phycoerythin-conjugated anti-CD14 antibody in the presence and absence of YO-PRO-1. The phycoerythrin signal is collected with a 585 nm filter with a 42 nm band pass (FL-2), whereas the YO-PRO-1 signal is collected with a 530 nm filter and a 30 nm band pass (FL-1). Using the results from the purified monocytes, the instrument is then set to trigger on the phycoerythrin signal by adjusting the acquisition threshold above the background associated from unlabeled cells. Thus, data from all non-phycoerythrin labeled cells are not acquired, and pilot experiments with the isotype control antibody documented that this threshold was specific for CD14$^+$ cells with forward and side scatter characteristics consistent with monocytes (unpublished data). Because the YO-PRO-1 signal is so intense, compensation was used to eliminate the YO-PRO-1 signal in the phycoerythrin channel. These standard settings were then used without adjustment for the remainder of the investigation. Whereas this enhances reproducibility of the inventors' study, it also contributes to day-to-day assay variability. The inventors therefore chose the Bz-ATP-induced fold-stimulation of YO-PRO-1 uptake as a measurement of P2X$_7$ pore activity in attempt to account for these systematic factors, as well as minimize the potential variability from P2X$_7$-independent sources of YO-PRO-1 uptake such as pinocytosis.

Quantification of plasma cytokine levels after ex vivo stimulation of whole blood with lipopolysaccharide. Aliquots of citrated whole blood (1 mL/aliquot) were stimulated with Hank's standard phosphate buffered saline (PBS) without calcium or magnesium in the presence and absence of *Salmonella typhimurium* lipopolysaccharide (LPS; 0.1 μg/mL; ATCC strain 14028, List Biologicals Inc., www.listlabs.com) for 6 hr at 37° C. with 5% CO$_2$. Plasma samples were collected after centrifugation, aliquoted, and stored at −80° C. Sandwich ELISA quantification of TNF-α, IL-1β, and IL-10 levels in diluted plasma was done with the OptEIA reagents for 20 plates (BD Biosciences) according to standard methods. Data from a custom Search Light cytokine array (Pierce Biotechnology, Rockford, Ill.) and the ArrayVision analysis software (v. 8.0, Imaging Research Inc., St. Catharines, Ontario, Canada) for these cytokines were also compared. Standard curves were generated with the provided recombinant cytokines mixed with assay diluent and an identical dilution of unstimulated citrated plasma. Each plate contained one or more sets of plasma samples with known cytokine concentrations. All subject samples were run in duplicate on the same plate.

Statistical analysis. A Chi-squared goodness of fit test (28) was used to determine whether the 1513 C allele frequency was in accordance with the principles of the Hardy Weinberg equilibrium (29). For flow cytometric experiments, data analysis was done as a batch using FlowJo software (v. 4.3; Tree Star, Inc., Palo Alto, Calif.) in order to apply the same CD14$^+$ analysis gates to the entire study. Monocytes take up fluorescent dyes by macropinocytotic mechanisms (evidenced by comparing the fluorescence associated with unstimulated monocytes in the presence and absence of YO-PRO-1, data not shown), and this process likely has variability within a large sample independent from P2X$_7$ (30). Thus, in order to make the measurements of dye uptake more reflective of P2X$_7$ pore activity, a "X"-fold stimulation was calculated using the ratio of the geometric mean of YO-PRO-1 fluorescence from 10,000 CD14$^+$ cells treated with Bz-ATP relative to the geometric mean fluorescence derived from 10,000 CD14$^+$ cells treated with the vehicle control.

The ratios of these means were entered in to one-way analysis of variance with three classes as determined by the A1513C genotype, followed by unpaired Student's t-tests with correction for unequal variance. In order to determine the lowest-fold stimulation of monocyte pore activity statistically different from the P2X$_7$ 1513 CC group, the standard deviation of pore activity in this group was multiplied by 2.41 (the t-statistic for six degrees of freedom), and this product was added to the group mean. By this method, high P2X$_7$ pore activity was defined as greater than 15-fold Bz-ATP-induced YO-PRO-1 uptake by CD14$^+$ cells, and low activity was established as less than or equal to 15-fold. Thus, any new subject with greater that 15-fold Bz-ATP-induced pore activity has a 95% chance of being statistically different than the group of subjects with the 1513 CC genotype.

For the cytokine portion of the study, subject assignment to the low or high pore activity group was verified by replication of the phase I monocyte pore assay on the day of phase II re-enrollment. Although one individual in the high pore group and three subjects with low activity crossed over the assignment threshold defined above, the cytokine data were analyzed by the intention to treat method such that the initial group designations from phase I were applied for all of the data. Regarding the cytokine comparisons between groups, unpaired Student's t-tests were again used with correction for unequal variance. All calculations were performed using Excel:Mac 2001, v. SR1 (Microsoft Corporation, Redmond, Wash.) with a p-value of 0.05 adopted as the threshold for significance.

Results

Figure 4:
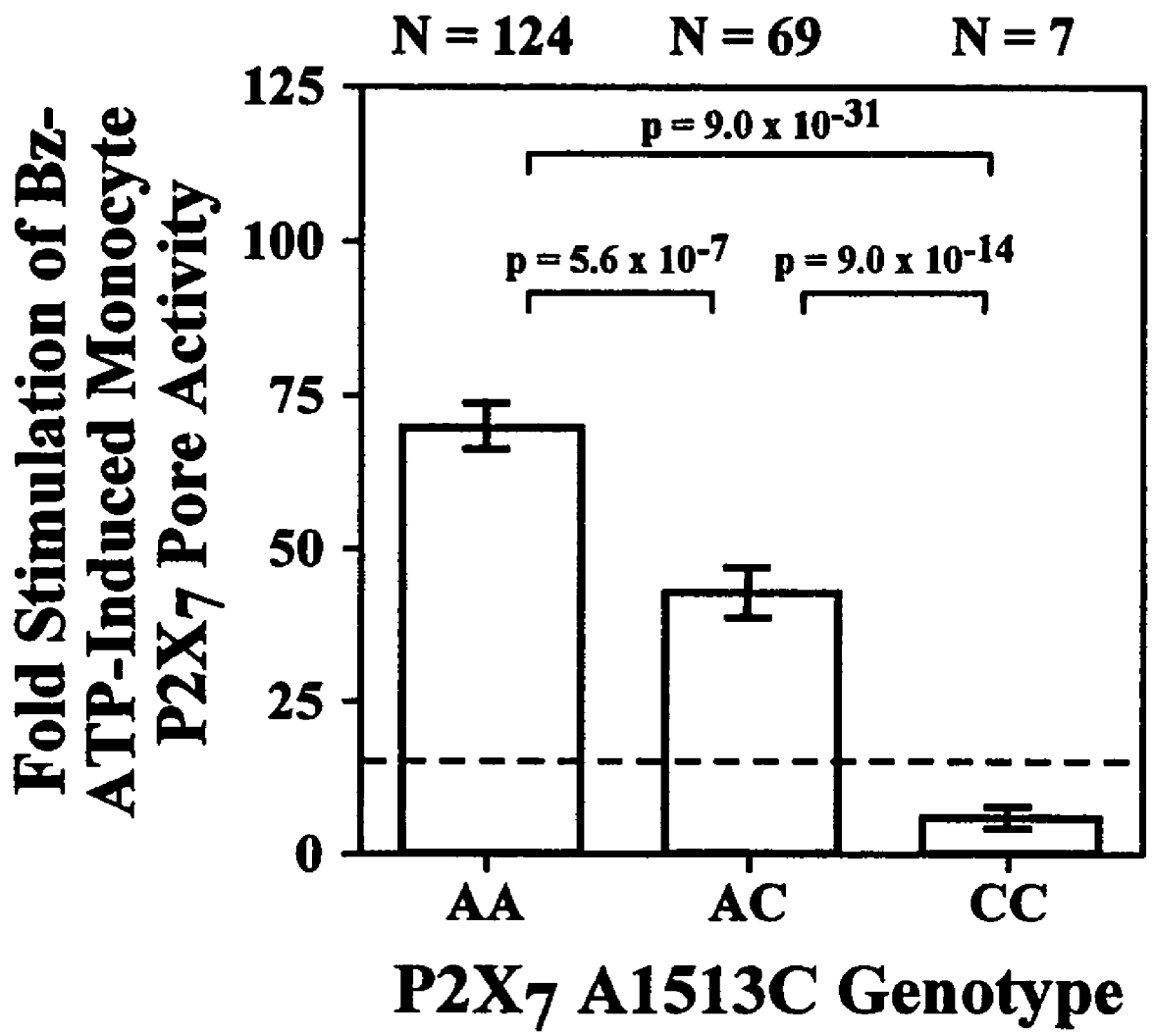
FIG. 4 illustrates $P2X_7$ pore activity in 200 healthy subjects separated according to the 1513 genotype. The ratios of Bz-ATP vs. control-stimulated YO-PRO-1 uptake in $CD14^+$ monocytes were calculated for 200 subjects on the day of Phase I enrollment as a selective measure of $P2X_7$ activity (see related Methods section). Data are separated according to the $P2X_7$ A1513C genotype, because this allele exhibits a predictable gene dosage effect when pore activity is measured by other methods (19). The group means and standard errors are shown along with the results of unpaired Student's t-tests with correction for unequal variance. The horizontal line depicts the statistically-defined separation between the high and low pore activity groups (see related Methods section).

Monocyte pore activity as a screen for individuals with P2X$_7$ genetic polymorphisms. In order to test the influence of various P2X$_7$ alleles on immune function, the inventors established a rapid screening assay sensitive to the presence of known polymorphisms. Although P2X$_7$ is expressed in most leukocytes, monocytes exhibit the greatest variability in pore activity (19). Previous methods used to study the P2X$_7$ pore activity in primary cells include the lysis of erythrocytes, the isolation of whole blood leukocytes by gradient centrifugation, or the purification of lymph node T cells (19,27). These techniques are too laborious for large phenotypic screens, and are confounded by the premature release of endogenous nucleotides as well as the potential for Percoll gradient-induced activation of monocytes by physical factors and/or contaminating LPS. By contrast, the labeling of whole blood with a CD14 specific antibody allowed for the use of a flow cytometry acquisition threshold technique to rapidly identify monocytes in these samples (FIG. 4), and dramatically reduced the potential for systematic variability associated with these isolation procedures. In order to maximize the differences in pore activity between the groups of subjects, the inventors implemented a long treatment time (20 min) at ambient temperature with a medium dose of a selective P2X$_7$ agonist (250 μM Bz-ATP) in the absence of sodium chloride, followed by pore closure at the end of the assay upon adjustment to 10 mM MgCl$_2$ before washing (18). These conditions selectively allowed for robust monocyte uptake of the fluorescent dye YO-PRO-1 in samples from 1513 AA subjects, with little to no P2X$_7$-stimulated activity associated with the CC genotype (FIG. 4).

For all subjects, the inventors measured the baseline fluorescence of CD14+cells in whole blood samples mixed with YO-PRO-1, and compared them to readings obtained after stimulation with 250 μM Bz-ATP. The basal YO-PRO-1 fluorescence associated with untreated CD14+ cells in whole blood had a coefficient of variance of 0.40 over the course of the study, approximately half of which was due to day-to-day assay variability. The inventors chose the Bz-ATP-induced fold stimulation of YO-PRO-1 uptake as a measurement of P2X$_7$ pore activity in attempt to account for these systematic factors, as well as minimize the potential variability from P2X$_7$-independent sources of YO-PRO-1 uptake such as pinocytosis.

With this rapid whole blood assay, the inventors screened two hundred healthy adults and correlated the results with the P2X$_7$ A1513C genotype, because gene dosage is known to predict pore activity measured by other methods (19). Sixty-nine AC heterozygous and seven CC homozygous individuals were identified, yielding a P2X$_7$ 1513 C allele frequency of 0.21 with a distribution in accordance with the Hardy-Weinberg equilibrium ($\chi^2=0.7$, $p>0.5$) (29). Despite conditions that favor the identification of low responders, the rapid pore assay produced average "X"-fold stimulations of monocyte pore activity that were statistically distinct for each group according to the P2X$_7$ 1513 genotype (FIG. 4). Notably, all samples taken from subjects with the variant CC genotype had relatively low inducible P2X$_7$-pore activity (FIG. 4). An analysis of variance demonstrated that there was significantly more pore assay variability between the genotypes compared to the variances within each group ($F=19.4$, $p=1\times10^{-8}$). The three t-test comparisons between the groups were significantly different (FIG. 4). Thus, the washed whole blood monocyte pore assay correctly identified all individuals with the P2X$_7$ 1513 CC genotype, and preserved the gene dosage effect previously described for the C allele (19).

Frequency of depressed monocyte pore activity in a healthy adult population, identification of individuals with other P2X$_7$ polymorphisms and performance of the whole blood pore assay. Given the results of the P2X$_7$ 1513 CC group, the inventors defined low monocyte pore activity statistically as less than or equal to fifteen-fold induction of Bz-ATP stimulated uptake of YO-PRO-1 (see the Statistical analysis section of the Methods). Using this threshold, twenty-three additional subjects had low pore activity despite their 1513 AA (n=11) or AC (n=12) genotypes, after confirmation of the latter results by sequence analysis of the PCR products from P2X$_7$ exon 13. This exon also contains a recently described single nucleotide polymorphism (T1729A) that confers an amino acid substitution (I568N) influencing the cell surface localization of the receptor (31).

Hence, eleven individuals in the low pore activity group were identified with the P2X$_7$ 1729 TA (but none with 1729 AA) genotype, nine of which were enrolled in the cytokine portion of the inventors' study (see below as well as Table 1). This was in keeping with its previously observed low allele frequency (0.02, ref(31)).

TABLE 1

| P2X$_7$ Pore Activity | P2X$_7$ A1513C genotype | P2X$_7$ T1729A genotype | # of subjects |
|---|---|---|---|
| high | AA | TT | 7 |
| high | AC | TT | 7 |
| low | AA | TT | 4 |
| low | AA | TA | 5 |
| low | AC | TT | 6 |
| low | AC | TA | 4 |
| low | CC | TT | 7 |

Referring to Table 1, P2X$_7$ genotype distribution for subjects enrolled in the LPS-induced cytokine study separated by pore activity are shown. Fourteen and twenty-six subjects were enrolled into Phase II of the study with high and low pore activity assignments and the genotypes were confirmed by sequence analysis of PCR products from exon 13. The latter group includes nineteen of the twenty-three Phase I subjects with low pore activity despite the presence of at least one 1513 A allele. The genotypes of the four subjects with low pore activity lost to follow up are AA/TT, AA/TA, AC/TT, and AC/TA; these four subjects are not included in the Table.

The 1513 C and the 1729 A P2X$_7$ polymorphisms segregated independently in the inventors' population; the 1729 A allele was equally present in individuals with the common 1513 AA and the heterozygote AC genotypes (n=6 and 5 respectively), and none of the 1513 CC subjects carried the 1729 A change. Interestingly, twelve individuals had low monocyte P2X$_7$ pore activity despite the presence of the common 1729 TT in conjunction with the absence of the variant 1513 CC genotypes. These data suggest the presence of yet to be disclosed-P2X$_7$ alleles and/or distinct genetic loci affecting nucleotide-stimulated monocyte pore activity.

Although the basal YO-PRO-1 fluorescence obviously affects the calculated Bz-ATP induced fold-stimulation of dye uptake, these values did not differ between the high and low pore activity groups (p=0.62). Evaluation of the distribution of baseline data and replacement of outlier baseline data (those greater than the mean±two standard deviations) with the group mean of unstimulated fluorescence showed that the calculation of fold-stimulation resulted in only one of two hundred subjects receiving an inappropriate pore activity group assignment. In sum, the whole blood pore assay accurately identified individuals with loss-of-function $P2X_7$ alleles.

Cytokine production by LPS-stimulated whole blood. The $P2X_7$ pore activity regulates the posttranslational activation of interleukin-1β via proteolytic cleavage (8,32). Additionally, pharmacological studies have linked $P2X_7$ activity to the modulation of the levels of a variety of NF-κB-dependent inflammatory cytokines and mediators (5,8,10,33). Hence, the inventors hypothesized that individuals with the 1513 CC genotype and/or low pore activity regardless of their $P2X_7$ genotype would produce less interleukin-1β or have an anti-inflammatory cytokine profile in response to lipopolysaccharide (LPS). To test this hypothesis, the inventors re-enrolled forty of the initial two hundred Phase I subjects; twenty-six from the low pore group and fourteen randomly selected controls with high activity and with equal representation of the 1513 AA and AC genotypes (Table 1). The pore assay group assignments from Phase I were reproducible for 36 of the 40 Phase II subjects staying below or above the 15-fold stimulation cut off and with collective intra-subject day-to-day coefficients of variance of 0.16 and 0.32 for the low and high groups respectively. Three subjects with low pore activity in Phase I had a 13, 45, and 57% increase in their Phase II pore assay results, whereas one subject with high Phase I pore activity had a 53% reduction on retesting such that the replicate result predicted the opposite group assignment in Phase II. In all cases, the Phase I group assignments were used for an intent-to-treat analysis of the cytokine data.

Figure 5:
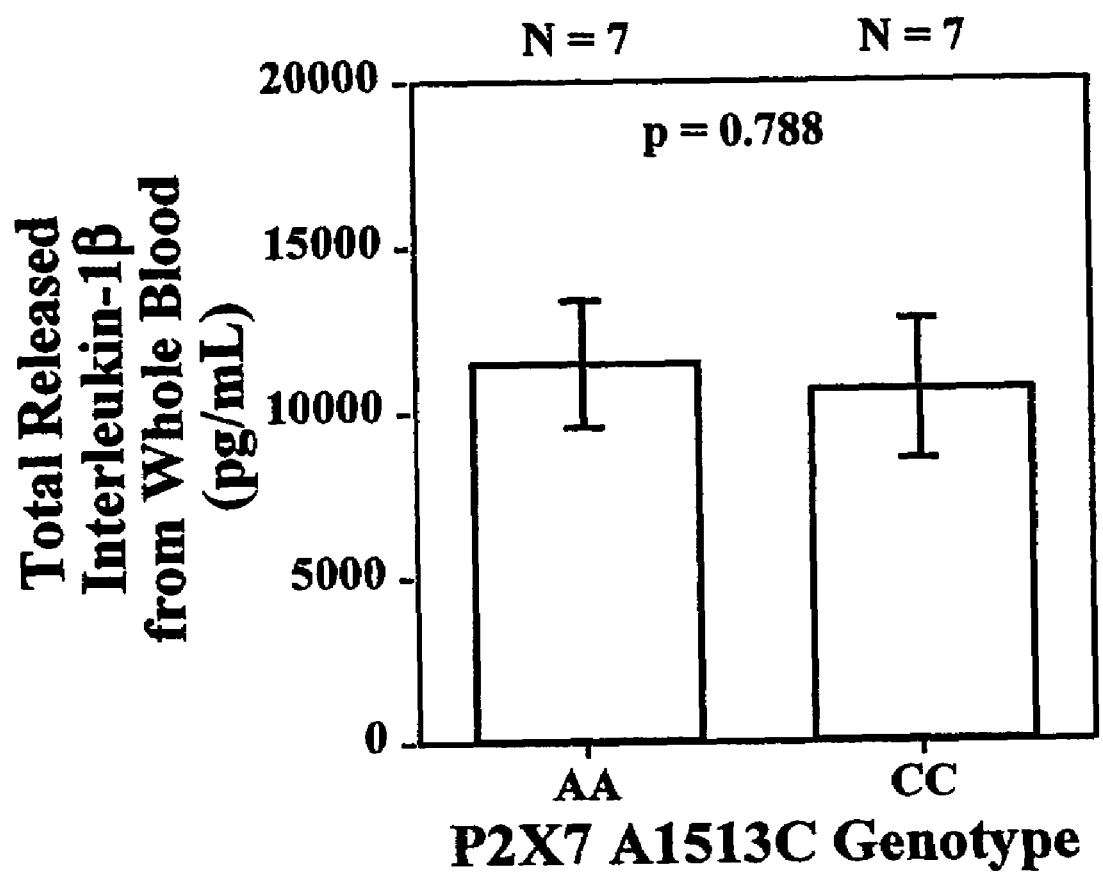
FIG. 5 depicts LPS-stimulated whole blood production of interleukin-1β. Whole blood samples from Phase II subjects were stimulated for 6 hr at 37° C. with 0 or 100 ng/mL of *Salmonella typhimurium* LPS followed by centrifugation to harvest plasma. The control samples contained undetectable levels of IL-1β. Subject samples were quantified by sandwich ELISA in duplicate, and the data shown are the group means and standard errors from seven subjects per group ($P2X_7$ 1513 AA/1729 TT vs. 1513 AA/1729 TT) combined from three experiments. Similar results were also seen using a cytokine array available from Pierce Biotechnology, Inc. under the trademark SEARCHLIGHT.

Whole blood samples were used to measure the cytokine responses in vitro after 6 hours of stimulation with zero or 100 ng/mL of *Salmonella typhimurium* LPS, as these conditions produce half-maximal responses in most donors (34-37). Additionally, LPS-stimulated platelets in whole blood are the source for abundant levels of endogenous adenine nucleotides (38) and the interaction between LPS-stimulated platelets and monocytes has been shown to augment the production of IL-1β (39). This method of LPS-stimulation of whole blood resulted in robust production of interleukin-1β plasma levels for all of the subjects regardless of genotype or $P2X_7$ pore activity, above an undetectable background in the saline-treated controls. There was no difference in the LPS-stimulated plasma IL-1β levels between subjects with the 1513 AA or CC genotype (FIG. 5). Combining data from the high and low pore activity subjects did not compress the variance sufficiently to reach statistical significance (9.9±1.4 and 8.4±0.7 ng/mL respectively, p=0.37).

However, because the plasma levels of tumor necrosis factor-α and interleukin-10 have been linked to the cytokine balance pertinent to a variety of inflammatory diseases (40-44), the inventors measured these two mediators as surrogates for the pro- vs. anti-inflammatory response profiles. Similar to the results with IL-1β, the saline-treated samples contained undetectable plasma levels of TNF-α and IL-10 for all but one of the subjects. By contrast, the samples from subjects with low $P2X_7$ monocyte pore activity had lower LPS-induced levels of TNF-α relative to the high pore activity group (FIG. 4). This coincided with higher levels of IL-10 in the low pore group (FIG. 6). When the TNF-α/IL-10 ratio was calculated on an individual subject basis, this measure for subjects with high pore activity was 264% greater on average than that of the low pore group (FIG. 6). Thus, the moncyte pore assay predicted the $P2X_7$ genotype, as well as the TNF-α/IL-10 ratio in response to whole blood treatment with LPS. With these mediators as surrogates, this suggests that individuals with low pore activity due to $P2X_7$ polymorphisms have an anti-inflammatory mediator profile in response to LPS.

The present investigation confirms the $P2X_7$ 1513 C allele frequency in a large sample, and extends these results to include individuals from North America. Previous studies have documented a 1513 C allele frequency of 0.09 in Gambians (45), 0.12 in Australians (19), and 0.14 in Swedes (46), in comparison to the inventors' findings of 0.21 in the Upper Midwest. The 1513 allele is more common than the $P2X_7$ 1729 polymorphism, with an estimated 1729 A allele frequency of 0.02 in Australians (31) and at least 0.03 in the inventors' sample. Coupled with the five other human $P2X_7$ promoter polymorphisms (47) and two murine structural variants, this genetic locus may be a region of greater variability than presently documented.

This is the largest study to date to evaluate the variability of $P2X_7$ function in monocytes. In particular, the inventors have developed a novel method for characterizing $P2X_7$ pore function with several distinct advantages. The antibody labeling and flow cytometric threshold techniques allow for the functional assessment of monocytes (or other cell types) using ≦1 mL of whole blood, an aspect that has tremendous significance regarding the potential for future use in an unstable, critically-ill patient population. With the existing method, results are available in less than three hours from the time of phlebotomy, making possible the design of immunomodulatory clinical trials with prospective stratification of patient subsets. Moreover, the technique is readily adaptable for use in a clinical lab of an average community hospital, broadening its applicability compared to previous methods.

In addition, the inventors demonstrated a subset of healthy subjects with discordance between their $P2X_7$ 1513 genotypes and monocyte pore activities. Twenty-three individuals in the inventors' sample had low pore activity despite the presence of at least one wild-type 1513 A allele (FIG. 4 and Table 1). Eleven of these twenty-three were 1729 TA heterozygotes, suggesting that at least twelve subjects in this study have yet to be disclosed polymorphisms affecting monocyte $P2X_7$ pore activity. In combination with the seven subjects with the 1513 CC genotype, these data demonstrate that 15% of individuals residing in the Upper Midwest of North America have low monocyte $P2X_7$-regulated pore function. With this frequency of reduced leukocyte activity among healthy individuals, it is unlikely that defects in the $P2X_7$ pore are associated with gross immunodeficiency, however, these alleles may contribute to the variability in the immune response when the system is under stress, such as during a major infection. A potential trade off might be enhanced microbial clearance at the expense of a higher incidence of autoimmune disorders and visa versa. Most candidate genes for these types of questions have multiple alleles, each with variable influence on protein function, inconsistent allele frequencies among distinct substrata of a given population, and unequal associations with clinical disease. Thus, functional tests, like the rapid monocyte pore assay, that are able to account for the influence of multiple alleles in linked pathways and to screen for polymorphisms at novel loci, are needed to assess the biological relevance of genetic variation in the pathogenesis of a given disease process.

In sum, the inventors have developed a rapid, washed whole blood pore assay that has numerous advantages over previous methods for detecting $P2X_7$ allele variants influencing pore activity. The pore assay, in addition to providing a rapid and reliable assay of pore activity, facilitates rapid identification of subjects with novel $P2X_7$ mutations. Characterization of these mutations will lead to additional polymorphic markers useful in determining correlation between allelic variants and clinical outcomes. Such recognition of prognostic determinants is extremely valuable in refining immunomodulatory and anti-infectious therapy on a patient-by-patient basis.

The antibody labeling and flow cytometric threshold techniques allow for the functional assessment of monocytes (or other cell types) using ≦1 mL of whole blood, an aspect that has tremendous significance regarding the potential for future use in an unstable, critically-ill patient population. Moreover, the technique is readily adaptable for use in a clinical lab of an average community hospital, broadening its applicability compared to previous methods. Because the results are available in less than three hours from the time of phlebotomy, the design of immunomodulatory clinical trials with prospective stratification of patient subsets is now possible. An underlying hypothesis for these trials would be that septic patients with attenuated monocyte $P2X_7$ pore activity would be relatively protected from organ dysfunction and shock, potentially at the expense of a diminished ability to control the infection locally or at increased susceptibility to certain classes (e.g. intracellular) of microbial pathogens.

Example 3

This example describes the identification of single nucleotide polymorphisms (SNPs) in human $P2X_7$ as facilitated by a functional assay according to the present invention. The frequency distribution of certain SNPs between low and high pore activity groups is supportive of the SNPs' utility as prognostic indicators of sepsis susceptibility.

As described in the previous example, two hundred healthy individuals were screened for $P2X_7$ phenotypes by a pore assay according to the invention. Based on the results, the population was classified into high and low pore activity groups. As discussed herein, persons with mutant $P2X_7$ genes resulting in low pore activity appear to have an elevated susceptibility to sepsis. Thus, a correlation of low pore activity with any given SNP is a marker for sepsis susceptibility. About 15% (30 people) of the 200 healthy individuals displayed depressed pore activity. Of the 30 people, 16 were identified as having previously known mutations; seven people had the A1513C mutation and nine people had the Ti 729 mutation, respectively. The remaining 19 individuals with low pore activity did not correlate with any previously known mutations in the $P2X_7$ gene. In order to characterize the molecular nature of these low pore activity cases, the inventors sequenced the $P2X_7$ gene from each of the relevant individuals to identify the presence of $P2X_7$ mutations. $P2X_7$ exons 1-13 were amplified by polymerase chain reaction (PCR) using exon-specific intronic primer pairs. Amplification reactions of individual exons 1-13 were generally-carried out under the following parameters: initial denaturation at 94° C. for 10 min followed by 35 cycles of denaturation at 94° C. for 1 min., annealing at 50-70° C. for 1 min., and extension at 72° C. for 10 min. Final reaction concentrations for exons 1-7 and 9-13 were: 1×PCR buffer II (supplied with enzyme), 1.5 mM $MgCl_2$, 200 uM each dNTPs, 0.4 uM Primer-Forward, 0.4 uM Primer-Reverse and 2.5 units/reaction Amplitaq Gold (Applied Biosystems). Final concentrations for reactions amplifying exon 8 were: 1×PCR buffer II (supplied with enzyme), 3.0 mM $MgCl_2$, 200 uM each dNTPs, 0.4 uM Primer-Forward, 0.4 uM Primer-Reverse and 2.5 units/reaction Amplitaq Gold (Applied Biosystems). Primers were generally 21-25mers designed by reference to human $P2X_7$ gene sequences which are publicly available (e.g., Accession nos. NM177427, NM002562, BC011913, Y12851, Y12852, Y12853, Y12854, Y12855, all sequences incorporated herein by reference).

Table 2 below illustrates SNPs identified by the present inventors during sequence analysis of $P2X_7$ genes of individuals from high pore and low pore activity groups, such groups being described in a previous example. Previously-known SNPs are indicated with a "+". SNPs identified in the present study which exhibit a frequency difference between individuals with high or low $P2X_7$ pore activity are indicated with an "*". The positions of SNPs in intronic sequences are indicated as either upstream of a bordering exon (position number is negative relative to exon's 5' end) or downstream of a bordering exon (position number is positive relative to exon's 3' end). Frequencies in low and high pore activity groups are indicated where they have been determined by the present inventors. Selected SNPs are further described in the following paragraph.

TABLE 2

| Exon | Base Change (position in cds or relative to exon)) | AA Change or relative intron position | Frequency among low pore activity individuals | Frequency among high pore activity individuals |
|---|---|---|---|---|
| 1 | G-->C (+42) | 3' intron | 18 WT (94.7%) 1 Het (5.3%) | |
| 4 | A-->G (-53) | 5' intron | 9 Het (47.4%) 10 Mut (52.6%) | |
| 5 | G474A | Gly150Arg | 16 WT (84.2%) 2 Het (10.5%) 1 Mut (5.3%) | 7 WT (87.5%) 1 Het (12.5%) |
| 5 | C489T | His155Tyr | 6 WT (31.6%) 10 Het (52.6%) 3 Mut (6.3%) | 2 WT (25%) 3 Het (37.5%) 3 Mut (37.5%) |
| 5 | C531T | Cys168Cys | 10 WT (52.6%) 9 Het (47.4%) | 8 WT (100%) |
| 5 | T-->C (-48) | 5' intron | 1 WT (5.3%) 12 Het (63.2%) 6 Mut (31.6%) | 8 Mut (100%) |
| 6 | A-->C (-107) | 5' intron | 9 Het (47.4%) 10 Mut (52.6%) | |
| 6 | C-->T (-42) | 5' intron | 9 Het (47.4%) 10 Mut (52.6%) | |
| 6 | C-->T (-38) | 5' intron | 9 Het (47.4%) 10 Mut (52.6%) | |
| 7 | Dup/Ins TTTG (-17) | 5' intron | 9 WT (47.4%) 10 Mut (52.6%) | |
| 7 | G-->C (-5) | 5' intron | 9 WT (47.4%) 10 Mut (52.6%) | |
| 8 | G835A | Arg270His | 14 WT (73.7%) 4 Het (21.1%) 1 Mut (5.3%) | 6 WT (75%) 1 Het (12.5) 1 Mut (12.5%) |
| 9 | G946A* | Arg307Gln | 16 WT (84.2%) 3 Het (15.8%) | 8 WT (100%) |
| 9 | GA-->AG (-2) | Glu-2Arg | 19 Mut (100%) | 8 Mut (100%) |
| 11 | A1068G* | Thr348Ala | 1 WT (5.3%) 0 Het (0%) 18 Mut (94.7%) | 3 Het (37.5%) 5 Mut (62.5%) |
| 11 | C1096G* | Thr357Ser | 10 WT (52.6%) 9 Het (47.4%) | 8 WT (100%) |
| 11 | C-->T (+34) | 3' intron | 1 WT (5.3%) 0 Het (0%) 18 Mut (94.7%) | |
| 12 | T1287C | Leu421Leu | 19 Mut (100%) | |
| 13 | T-->C (-85) | 5' intron | 1 WT (5.3%) 0 Het (0%) 18 Mut (94.7%) | 8 Het (38.1%), 13 Mut (61.9%) |
| 13 | G-->A (-84) | 5' intron | 15 WT (78.9%) 3 Het (15.8%) 1 Mut (5.3%) | 19 WT (90.5%) 2 Het (9.5%) |
| 13 | A1469C | Arg481Ser | 19 Mut (100%) | 21 Mut (100%) |
| 13 | A1772G | Pro582Pro | 1 WT (5.3%) 0 Het (0%) 18 Mut (94.7%) | 1 WT (4.8%) 7 Het (33.3%) 13 Mut (61.9%) |
| 13 | A1513C+ | Glu496Ala | 9 WT (47.4%) 10 Het (52.6%) | 9 WT (42.9%) 5 Het (23.8%) 7 Mut (33.3%) |

TABLE 2-continued

| Exon | Base Change (position in cds or relative to exon)) | AA Change or relative intron position | Frequency among low pore activity individuals | Frequency among high pore activity individuals |
|---|---|---|---|---|
| 13 | A1405G* | Gln460Arg | 18 WT (94.7%) 1 Het (5.3%) | 16 WT (76.2%) 5 Het (23.8%) |
| 13 | G1628T | Leu534Leu | 9 WT (47.4%) 10 Het (52.6%) | 19 WT (90.5%) 2 Het (10.5%) |
| 13 | T1729A+ | Ile568Asn | 10 WT (52.6%) 9 Het (47.4%) | 21 WT (100%) |
| 13 | C1448T | Pro474Pro | 10 WT (52.6%) 9 Het (47.4%) | 20 WT (95.2%) 1 Het (4.8%) |

Several SNPs depicted in Table 2 above are further detailed below and are particularly useful as prognostic indicators, the use of such being described in a previous section.

Sequence analysis of PCR fragments corresponding to exon 9 revealed a previously-undescribed G to A transition at nucleotide position 946 resulting in an R307Q mutation in the $P2X_7$ amino acid sequence. This SNP was not present in eight high pore activity individuals sampled but was heterozygous in three of nineteen low pore activity individuals. Therefore, this SNP was present in low pore activity activity individuals sampled at a 15.8% frequency as compared to 0% frequency in high pore activity individuals.

A second, previously-undescribed SNP was located in exon 11 wherein an A to G transition at nucleotide position 1068 resulted in a T348A mutation in corresponding amino acid sequence. In eight high pore activity individuals sampled, this SNP was heterozygous in three individuals and homozygous in the remaining five. In nineteen low pore activity individuals, this SNP was absent in one individual, and homozygous in the remaining eighteen (94.7% frequency among low pore activity individuals).

A third SNP was identified in exon 11 wherein a C to G transversion at nucleotide position 1096 resulted in a T357S mutation in the corresponding polypeptide. In eight high pore activity individuals sampled, this SNP was not present. In contrast, of nineteen low pore activity individuals assayed, this SNP was heterozygous in nine individuals. Thus, the SNP was present at a 47.4% frequency sampled low pore activity individuals as compared to 0% of high pore activity individuals.

A fourth SNP was identified in exon 13 wherein an A to G transition at nucleotide position 1405 resulted in a Q460R mutation in the respective polypeptide. In twenty one high pore activity individuals sampled, the SNP was not present in sixteen of the individuals and heterozygous in five. In nineteen low pore activity individuals, the SNP was not present in eighteen individuals and heterozygous in the remaining individual. Therefore, the frequency of the SNP was different between groups with it being present in 23.8% of high pore activity individuals sampled but only 5.3% of low pore activity individuals sampled.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and other written materials cited herein are hereby incorporated by reference in their entirety for all purposes.

IV. REFERENCES

1. Bone, R. C., C. J. Grodzin, and R. A. Balk. Sepsis: a new hypothesis for pathogenesis of the disease process. *Chest* 112(1):235-43 (1997).
2. Angus, D. C., W. T. Linde-Zwirble, J. Lidicker, G. Clermont, J. Carcillo, and M. R. Pinsky. Epidemiology of severe sepsis in the United States: analysis of incidence, outcome, and associated costs of care. *Crit Care Med* 29(7):1303-10. (2001).
3. Rivers, E., B. Nguyen, S. Havstad, J. Ressler, A. Muzzin, B. Knoblich, E. Peterson, and M. Tomlanovich. Early goal-directed therapy in the treatment of severe sepsis and septic shock. *N Engl J Med* 345(19):1368-77. (2001).
4. Angus, D. C., and R. S. Wax. Epidemiology of sepsis: an update. *Crit Care Med* 29(7 Suppl):S109-16. (2001).
5. Watters, J. J., J. A. Sommer, P. L. Fisette, Z. A. Pfeiffer, M. Aga, U. Prabhu, A. Guerra, L. C. Denlinger, and P. J. Bertics. The P2X7 nucleotide receptor: Modulation of LPS-induced macrophage signaling and mediator production. *Drug Develop. Res.* 53:91-104 (2001).
6. Di Virgilio, F., P. Chiozzi, D. Ferrari, S. Falzoni, J. M. Sanz, A. Morelli, M. Torboli, G. Bolognesi, and O. R. Baricordi. Nucleotide receptors: an emerging family of regulatory molecules in blood cells. *Blood* 97(3):587-600. (2001).
7. Proctor, R. A., L. C. Denlinger, P. S. Leventhal, S. K. Daugherty, J. W. van de Loo, T. Tanke, G. S. Firestein, and P. J. Bertics. Protection of mice from endotoxi death by 2-methylthio-ATP. *Proceedings of the National Academy of Sciences of the United States of America* 91(13):6017-20 (1994).
8. Tonetti, M., L. Sturla, M. Giovine, U. Benatti, and A. De Flora. Extracellular ATP enhances mRNA levels of nitric oxide synthase and TNF-alpha in lipopolysaccharide-treated RAW 264.7 murine macrophages. *Biochemical & Biophysical Research Communications* 214(1):125-30 (1995).
9. Denlinger, L. C., P. L. Fisette, K. A. Garis, G. Kwon, A. Vazquez-Torres, A. D. Simon, B. Nguyen, R. A. Proctor, P. J. Bertics, and J. A. Corbett. Regulation of inducible nitric oxide synthase expression by macrophage purinoreceptors and calcium. *J Biol Chem* 271(1):337-42 (1996).
10. Hu, Y., P. L. Fisette, L. C. Denlinger, A. G. Guadarrama, J. A. Sommer, R. A. Proctor, and P. J. Bertics. Purinergic receptor modulation of lipopolysaccharide signaling and inducible nitric-oxide synthase expression in RAW 264.7 macrophages. *Journal of Biological Chemistry* 273(42):27170-5 (1998).
11. Solle, M., J. Labasi, D. G. Perregaux, E. Stam, N. Petrushova, B. H. Koller, R. J. Griffiths, and C. A. Gabel. Altered cytokine production in mice lacking P2X(7) receptors. *J Biol Chem* 276(1):125-32. (2001).
12. Aga, M., A. P. Hart, A. G. Guadarrama, C. J. Johnson, M. Suresh, J. P. Svaren, P. J. Bertics, and B. J. Darien. Modulation of Monocyte Signaling and Pore Formation in Response to Agonists of the Nucleotide Receptor P2×7. *J Leukocyte Biol.* 72:222-232 (2002).
13. Fairbairn, I. P., C. B. Stober, D. S. Kumararatne, and D. A. Lammas. ATP-mediated killing of intracellular mycobacteria by macrophages is a P2X(7)-dependent process inducing bacterial death by phagosome-lysosome fusion. *J Immunol* 167(6):3300-7. (2001).

14. MacKenzie, A., H. L. Wilson, E. Kiss-Toth, S. K. Dower, R. A. North, and A. Surprenant. Rapid secretion of interleukin-1beta by microvesicle shedding. *Immunity* 15(5): 825-35. (2001).

15. Di Virgilio, F., S. Falzoni, P. Chiozzi, J. M. Sanz, D. Ferrari, and G. N. Buell. ATP receptors and giant cell formation. *J Leukoc Biol* 66(5):723-6. (1999).

16. Surprenant, A., F. Rassendren, E. Kawashima, R. A. North, and G. Buell. The cytolytic P2Z receptor for extracellular ATP identified as a P2X receptor (P2×7). *Science* 272(5262):735-8. (1996).

17. Gu, B. J., W. Y. Zhang, L. J. Bendall, I. P. Chessell, G. N. Buell, and J. S. Wiley. Expression of P2X(7) purinoceptors on human lymphocytes and monocytes: evidence for non-functional P2X(7) receptors. *Am J Physiol Cell Physiol* 279(4):C1189-97. (2000).

18. Gudipaty, L., B. D. Humphreys, G. Buell, and G. R. Dubyak. Regulation of P2X(7) nucleotide receptor function in human monocytes by extracellular ions and receptor density. *Am J Physiol Cell Physiol* 280(4):C943-53. (2001).

19. Gu, B. J., W. Zhang, R. A. Worthington, R. Sluyter, P. Dao-Ung, S. Petrou, J. A. Barden, and J. S. Wiley. A Glu-496 to Ala Polymorphism Leads to Loss of Function of the Human P2X7 Receptor. *J Biol Chem* 276(14): 11135-11142. (2001).

20. Denlinger, L. C., P. L. Fisette, J. A. Sommer, J. J. Watters, U. Prabhu, G. R. Dubyak, R. A. Proctor, and P. J. Bertics. Cutting Edge: The Nucleotide Receptor P2X7 Contains Multiple Protein- and Lipid-Interaction Motifs Including a Potential Binding Site for Bacterial Lipopolysaccharide. *J Immunol* 167:1871-1876 (2001).

21. Lamping, N., A. Hoess, B. Yu, T. C. Park, C. J. Kirschning, D. Pfeil, D. Reuter, S. D. Wright, F. Herrmann, and R. R. Schumann. Effects of site-directed mutagenesis of basic residues (Arg 94, Lys 95, Lys 99) of lipopolysaccharide (LPS)-binding protein on binding and transfer of LPS and subsequent immune cell activation. *J Immunol* 157(10): 4648-56. (1996).

22. Humphreys, B. D., and G. R. Dubyak. Induction of the P2z/P2X7 nucleotide receptor and associated phospholipase D activity by lipopolysaccharide and IFN-gamma in the human THP-1 monocytic cell line. *J Immunol* 157(12): 5627-37. (1996).

23. Poussin, C., M. Foti, J. L. Carpentier, and J. Pugin. CD14-dependent endotoxin internalization via a macropinocytic pathway. *J Biol Chem* 273(32):20285-91. (1998).

24. Vasselon, T., E. Hailman, R. Thieringer, and P. A. Detmers. Internalization of monomeric lipopolysaccharide occurs after transfer out of cell surface CD14. *J Exp Med* 190(4):509-21. (1999).

25. Teasdale, R. D., and M. R. Jackson. Signal-mediated sorting of membrane proteins between the endoplasmic reticulum and the golgi apparatus. *Annu Rev Cell Dev Biol* 12:27-54 (1996).

26. Royle, S. J., L. K. Bobanovic, and R. D. Murrell-Lagnado. Identification of a non-canonical tyrosine-based endocytic motif in an ionotropic receptor. *J Biol Chem* 8:8 (2002).

27. Adriouch, S., C. Dox, V. Welge, M. Seman, F. Koch-Nolte, and F. Haag. 2002. Cutting edge: a natural P451L mutation in the cytoplasmic domain impairs the function of the mouse P2X7 receptor. *Journal of Immunology.* 169:4108.

28. Snedecor, G. W., and W. G. Cochran. 1989. *Statistical Methods.* Iowa State Univeristy Press, Ames.

29. Cannings, C., and A. W. Edwards. 1969. Expected genotypic frequencies in a small sample: deviation from Hardy-Weinberg equilibrium. *American Journal of Human Genetics.* 21:245.

30. Kitchens, R. L., P. Wang, and R. S. Munford. 1998. Bacterial lipopolysaccharide can enter monocytes via two CD14-dependent pathways. *Journal of Immunology.* 161: 5534.

31. Wiley, J. S., L. P. Dao-Ung, C. Li, A. N. Shemon, B. J. Gu, M. L. Smart, S. J. Fuller, J. A. Barden, S. Petrou, and R. Sluyter. 2003. An Ile-568 to Asn polymorphism prevents normal trafficking and function of the human P2X7 receptor. *Journal of Biological Chemistry.* 278:17108.

32. Mehta, V. B., J. Hart, and M. D. Wewers. 2001. ATP-stimulated release of interleukin (IL)-1beta and IL-18 requires priming by lipopolysaccharide and is independent of caspase-1 cleavage. *J Biol Chem* 276:3820.

33. Ferrari, D., S. Wesselborg, M. K. A. Bauer, and K. Schulze-Osthoff. 1997. Extracellular ATP activates transcription factor NF-kappaB through the P2Z purinoreceptor by selectively targeting NF-kappaB p65. *Journal of Cell Biology* 139:1635.

34. DeForge, L. E., J. S. Kenney, M. L. Jones, J. S. Warren, and D. G. Remick. 1992. Biphasic production of IL-8 in lipopolysaccharide (LPS)-stimulated human whole blood. Separation of LPS- and cytokine-stimulated components using anti-tumor necrosis factor and anti-IL-1 antibodies. *J Immunol* 148:2133.

35. Nerad, J. L., J. K. Griffiths, J. W. Van der Meer, S. Endres, D. D. Poutsiaka, G. T. Keusch, M. Bennish, M. A. Salam, C. A. Dinarello, and J. G. Cannon. 1992. Interleukin-1beta (IL-1beta), IL-1 receptor antagonist, and TNF alpha production in whole blood. *J Leukoc Biol* 52:687.

36. Dedrick, R. L., and P. J. Conlon. 1995. Prolonged expression of lipopolysaccharide (LPS)-induced inflammatory genes in whole blood requires continual exposure to LPS. *Infect Immun* 63:1362.

37. Frieling, J. T., J. A. Mulder, T. Hendriks, J. H. Curfs, C. J. van der Linden, and R. W. Sauerwein. 1997. Differential induction of pro- and anti-inflammatory cytokines in whole blood by bacteria: effects of antibiotic treatment. *Antimicrob Agents Chemother* 41:1439.

38. Timmons, S., A. Huzoor, J. Grabarek, M. Kloczewiak, and J. Hawiger. 1986. Mechanism of human platelet activation by endotoxic glycolipid-bearing mutant Re595 of *Salmonella* minnesota. *Blood* 68:1015.

39. Aiura, K., B. D. Clark, C. A. Dinarello, N. H. Margolis, G. Kaplanski, J. F. Burke, R. G. Tompkins, and J. A. Gelfand. 1997. Interaction with autologous platelets multiplies interleukin-1 and tumor necrosis factor production in mononuclear cells. *J Infect Dis* 175:123.

40. Sfeir, T., D. C. Saha, M. Astiz, and E. C. Rackow. 2001. Role of interleukin-10 in monocyte hyporesponsiveness associated with septic shock. *Critical Care Medicine.* 29:129.

41. Gogos, C. A., E. Drosou, H. P. Bassaris, and A. Skoutelis. 2000. Pro-versus anti-inflammatory cytokine profile in patients with severe sepsis: a marker for prognosis and future therapeutic options. *Journal of Infectious Diseases.* 181:176.

42. Rudwaleit, M., Z. Yin, S. Siegert, M. Grolms, A. Radbruch, J. Braun, and J. Sieper. 2000. Response to methotrexate in early rheumatoid arthritis is associated with a decrease of T cell derived tumour necrosis factor alpha, increase of interleukin 10, and predicted by the initial concentration of interleukin 4. *Annals of the Rheumatic Diseases.* 59:311.

43. Saiki, T., K. Mitsuyama, A. Toyonaga, H. Ishida, and K. Tanikawa. 1998. Detection of pro- and anti-inflammatory cytokines in stools of patients with inflammatory bowel disease. *Scandinavian Journal of Gastroenterology.* 33:616.

44. Westendorp, R. G., J. A. M. Langermans, T. W. J. Huizinga, A. H. Elouali, C. L. Verweij, D. I. Boomsma, and J. P. Vandenbrouke. 1997. Genetic influence on cytokine production and fatal meningococcal disease. *Lancet* 349:170.

45. Li, C. M., S. J. Campbell, D. S. Kumararatne, R. Bellamy, C. Ruwende, K. P. McAdam, A. V. Hill, and D. A. Lammas. 2002. Association of a polymorphism in the P2X7 gene with tuberculosis in a Gambian population. *Journal of Infectious Diseases.* 186:1458.

46. Thunberg, U., G. Tobin, A. Johnson, O. Soderberg, L. Padyukov, M. Hultdin, L. Klareskog, G. Enblad, C. Sundstrom, G. Roos, and R. Rosenquist. 2002. Polymorphism in the P2X7 receptor gene and survival in chronic lymphocytic leukaemia.[comment]. *Lancet.* 360:1935.

47. Li, C. M., S. J. Campbell, D. S. Kumararatne, A. V. Hill, and D. A. Lammas. 2002. Response heterogeneity of human macrophages to ATP is associated with P2X7 receptor expression but not to polymorphisms in the P2RX7 promoter. *FEBS Letters.* 531:127.

48. Wiley, J. S., L. P. Dao-Ung, B. J. Gu, R. Sluyter, A. N. Shemon, C. Li, J. Taper, J. Gallo, and A. Manoharan. 2002. A loss-of-function polymorphic mutation in the cytolytic P2X7 receptor gene and chronic lymphocytic leukaemia: a molecular study. *Lancet.* 359:1114.

49. Lammas, D. A., C. Stober, C. J. Harvey, N. Kendrick, S. Panchalingam, and D. S. Kumararatne. 1997. ATP-induced killing of mycobacteria by human macrophages is mediated by purinergic P2Z(P2x7) receptors. *Immunity.* 7:433.

50. Ferrari, D., P. Chiozzi, S. Falzoni, S. Hanau, and F. Di Virgilio. 1997. Purinergic modulation of interleukin-1beta release from microglial cells stimulated with bacterial endotoxin. *J Exp Med* 185:579.

51. Beigi, R. D., and G. R. Dubyak. 2000. Endotoxin activation of macrophages does not induce ATP release and autocrine stimulation of P2 nucleotide receptors. *J Immunol* 165:7189.

52. Sluyter, R., A. N. Shemon, and J. S. Wiley. 2004. Glu496 to Ala polymorphism in the P2X7 receptor impairs ATP-induced IL-1 release from human monocytes. *J Immunol* 172:3399.

53. Wewers, M. D., A. V. Winnard, and H. A. Dare. 1999. Endotoxin-stimulated monocytes release multiple forms of IL-1beta, including a proIL-1beta form whose detection is affected by export. *Journal of Immunology.* 162:4858.

54. Hide, I., M. Tanaka, A. Inoue, K. Nakajima, S. Kohsaka, K. Inoue, and Y. Nakata. 2000. Extracellular ATP triggers tumor necrosis factor-alpha release from rat microglia. *Journal of Neurochemistry.* 75:965.

55. Wilkin, F., P. Stordeur, M. Goldman, J. M. Boeynaems, and B. Robaye. 2002. Extracellular adenine nucleotides modulate cytokine production by human monocyte-derived dendritic cells: dual effect on IL-12 and stimulation of IL-10. *European Journal of Immunology.* 32:2409.

56. Hasko, G., D. G. Kuhel, A. L. Salzman, and C. Szabo. 2000. ATP suppression of interleukin-12 and tumour necrosis factor-alpha release from macrophages. *British Journal of Pharmacology.* 129:909.

57. Budagian, V., E. Bulanova, L. Brovko, Z. Orinska, R. Fayad, R. Paus, and S. Bulfone-Paus. 2003. Signaling through P2X7 receptor in human T cells involves p561ck, MAP kinases, and transcription factors AP-1 and NF-kappa B. *Journal of Biological Chemistry.* 278:1549.

58. Ferrari, D., C. Stroh, and K. Schulze-Osthoff. 1999. P2×7/P2Z purinoreceptor-mediated activation of transcription factor NFAT in microglial cells. *Journal of Biological Chemistry* 274:13205.

59. Qi, H., T. L. Denning, and L. Soong. 2003. Differential induction of interleukin-10 and interleukin-12 in dendritic cells by microbial toll-like receptor activators and skewing of T-cell cytokine profiles. *Infection & Immunity.* 71:3337.

60. Labasi, J. M., N. Petrushova, C. Donovan, S. McCurdy, P. Lira, M. M. Payette, W. Brissette, J. R. Wicks, L. Audoly, and C. A. Gabel. 2002. Absence of the P2X7 receptor alters leukocyte function and attenuates an inflammatory response. *Journal of Immunology.* 168:6436.

61. Li, C. M., S. J. Campbell, D. S. Kumararatne, R. Bellamy, C. Ruwende, K. P. McAdam, A. V. Hill, and D. A. Lammas. 2002. Association of a polymorphism in the P2X7 gene with tuberculosis in a Gambian population. *Journal of Infectious Diseases.* 186:1458.

What is claimed is:

1. A kit for measuring a nucleotide receptor P2X7 pore activity in white blood cells contained within a whole blood sample of a subject, the kit comprising:
   (a) a white blood cell-specific antibody conjugated to a label configured for labeling white blood cells contained within the subject's whole blood sample;
   (b) a dye capable of uptake by nucleotide receptor P2X7 pores;
   (c) a P2X7 agonist in an amount sufficient to activate nucleotide receptor P2X7 pore activity in the white blood cells contained within the subject's whole blood sample;
   (d) an isotonic depolarizing solution for depolarizing the labeled white blood cells: and
   (e) instructional material describing labeling white blood cells contained within the whole blood sample with the white blood cell-specific antibody conjugated to a label; depolarizing the labeled white blood cells with the isotonic depolarizing solution; contacting the labeled white blood cells with the dye and the P2X7 agonist in an amount sufficient to activate nucleotide receptor P2X7 pore activity;
   deactivating nucleotide receptor P2X7 pore activity; and analyzing dye uptake in the labeled white blood cells whereby nucleotide receptor P2X7 pore activity is quantified by the amount of dye taken up in labeled white blood cells treated with the P2X7 agonist relative to labeled white blood cells in the absence of said P2X7 agonist.

2. The kit according to claim 1 wherein the white blood cell-specific antibody conjugated to a label is a phycoerythrin-conjugated anti-CD14 antibody.

3. The kit according to claim 1 wherein the isotonic depolarizing solution comprises glutamate ion with the proviso that sodium and chloride ions and divalent cations are absent from said isotonic depolarizing solution in amounts effective to inhibit P2X7 pore activity.

4. The kit according to claim 1 wherein the dye is a DNA-binding dye having a mass of less than approximately 900 Daltons.

5. The kit according to claim 4 wherein said DNA-binding dye is YO-PRO-1.

6. The kit according to claim 1 wherein the P2X7 agonist is selected from the group consisting of 2'-3'-O-(4-benzoyl)-adenosine 5'-triphosphate (Bz-ATP), adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5'(beta,gamma-imido)triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof.

7. The kit according to claim 1 further comprising a divalent cation in an amount sufficient to deactivate nucleotide receptor P2X7 pore activity in the white blood cells contained within the subject's blood sample.

8. The kit according to claim 7 wherein the divalent cation is magnesium ion.

9. The kit according to claim 1 wherein said instructional material further comprises a decision tree which, based on at least the nucleotide receptor P2X7 pore activity measured by said kit, directs a user to a subject-specific clinical pathway of medical intervention for said subject.

10. The kit according to claim 1 wherein said instructional material describes the analysis of dye uptake by flow cytometry, wherein said flow cytometry detects labeled white blood cells apart from non-labeled cells in whole blood and measures intensity of the dye taken up by the labeled white blood cells whereby nucleotide receptor P2X7 pore activity is quantified by the amount of dye taken up in labeled white blood cells in the absence of said P2X7 agonist.

11. A method of assaying nucleotide receptor P2X7 pore activity in white blood cells contained within a blood sample, comprising the steps of:
    (a) labeling white blood cells contained within the blood sample with a white blood cell-specific antibody conjugated to a label;
    (b) depolarizing the labeled white blood cells with an isotonic depolarizing solution;
    (c) contacting the labeled white blood cells with a dye and a P2X7 agonist in an amount sufficient to activate nucleotide receptor P2X7 pore activity;
    (d) contacting the labeled white blood cells of step (c) with a divalent cation in an amount sufficient to deactivate nucleotide receptor P2X7 pore activity; and
    (e) analyzing dye uptake in the labeled white blood cells of step (d) whereby nucleotide receptor P2X7 pore activity is quantified by the amount of dye taken up in labeled white blood cells treated with the P2X7 agonist relative to labeled white blood cells in the absence of said P2X7 agonist.

12. A method according to claim 11 wherein the white blood cell-specific antibody conjugated to a label is a phycoerythrin-conjugated anti-CD 14 antibody.

13. A method according to claim 11 wherein the isotonic depolarizing solution comprises glutamate ion with the proviso that sodium and chloride ions and divalent cations are absent from said isotonic depolarizing solution in amounts effective to inhibit P2X7 pore activity.

14. A method according to claim 11 wherein the dye is a DNA-binding dye having a mass of less than approximately 900 Daltons.

15. A method according to claim 14 wherein said DNA-binding dye is YO-PRO-1.

16. A method according to claim 11 wherein the P2X7 agonist is selected from the group consisting of 2'-3'-O-(4-benzoyl)-adenosine 5'-triphosphate (Bz-ATP), adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5'(beta,gamma-imido)triphosphate (AMPPNP), adenosine 5'-diphosphate (ADP), 2-methylthio -adenosine 5'-diphosphate (2-MeS-ADP), 2-chloro-adenosine 5'-diphosphate (2-Cl-ADP) and mixtures thereof.

17. A method according to claim 11 wherein the divalent cation is magnesium ion.

18. A method according to claim 11 wherein dye uptake in step (e) is measured by flow cytometry.

19. A method according to claim 18 wherein said flow cytometry detects labeled white blood cells apart from non-labeled in wholo blood cells and measures intensity of the dye taken up by the labeled white blood cells whereby nucleotide receptor P2X7 pore activity is quantified by the amount of dye taken up in labeled white blood cells in the absence of said P2X7 agonist.

* * * * *

UNITED STATES PATENT AND TRADEMARK OFFICE
CERTIFICATE OF CORRECTION

PATENT NO. : 7,560,243 B2 Page 1 of 1
APPLICATION NO. : 10/827718
DATED : July 14, 2009
INVENTOR(S) : Loren C. Denlinger et al.

It is certified that error appears in the above-identified patent and that said Letters Patent is hereby corrected as shown below:

Column 1, Line 14 "This work was supported in part by grants from the National Institutes of Health AI 34891. The Government of the United States of America may have certain rights in this invention." should be -- This invention was made with United States government support awarded by the following agencies: NIH AI50500. The United States government has certain rights in this invention. --

Column 2, Line 23 "Ti 729A" should be -- T1729A --

Column 2, Line 40 "A1 513C" should be -- A1513C --

Column 5, Line 24 "BseRI" should be -- BseR I --

Column 10, Line 51 "530 m" should be -- 530 nm --

Column 13, Line 26 "fairbaim" should be -- Fairbairn --

Column 16, Line 36 "42 m" should be -- 42 nm --

Column 17, Line 28 "BseRI" should be -- BseR I --

Column 18, Line 60 "BseRI" should be -- BseR I --

Column 18, Line 63 "BseRI" should be -- BseR I --

Column 22, Line 15 "1568N" should be -- I568N --

Column 25, Line 41-42 "Ti729" should be -- T1729 --

Signed and Sealed this

Eighteenth Day of May, 2010

David J. Kappos
*Director of the United States Patent and Trademark Office*